(12) United States Patent
Lewis et al.

(10) Patent No.: US 7,820,753 B2
(45) Date of Patent: Oct. 26, 2010

(54) BLOCK COPOLYMERS

(75) Inventors: Andrew Lennard Lewis, Farnham (GB); Steven Peter Armes, Hassocks (GB); Yinghua Ma, Croydon (GB)

(73) Assignee: Biocompatibles UK Limited, Surrey (GB)

( * ) Notice: Subject to any disclaimer, the term of this patent is extended or adjusted under 35 U.S.C. 154(b) by 1422 days.

(21) Appl. No.: 10/544,113

(22) PCT Filed: Feb. 5, 2004

(86) PCT No.: PCT/GB2004/000449

§ 371 (c)(1),
(2), (4) Date: Aug. 2, 2005

(87) PCT Pub. No.: WO2004/069888

PCT Pub. Date: Aug. 19, 2004

(65) Prior Publication Data
US 2006/0069203 A1 Mar. 30, 2006

(30) Foreign Application Priority Data
Feb. 5, 2003 (EP) ................... 03250730

(51) Int. Cl.
*C08L 31/02* (2006.01)
(52) U.S. Cl. ........................ 524/556; 526/319
(58) Field of Classification Search ............... 524/556, 524/319
See application file for complete search history.

(56) References Cited

U.S. PATENT DOCUMENTS

| | | | |
|---|---|---|---|
| 5,441,841 A | 8/1995 | Larson et al. | |
| 6,395,800 B1 | 5/2002 | Jones et al. | |
| 6,852,816 B2 * | 2/2005 | Lewis et al. | 526/277 |
| 7,300,990 B2 | 11/2007 | Lewis et al. | |
| 2005/0123501 A1 | 6/2005 | Lewis | |
| 2005/0163743 A1 | 7/2005 | Lewis | |
| 2005/0220880 A1 | 10/2005 | Lewis | |
| 2006/0135714 A1 | 6/2006 | Lewis | |

FOREIGN PATENT DOCUMENTS

| | | |
|---|---|---|
| WO | WO 00/71660 A1 | 11/2000 |
| WO | WO 01/01957 A1 | 1/2001 |
| WO | WO 01/09208 A1 | 2/2001 |
| WO | WO 01/27209 A1 | 4/2001 |
| WO | WO 02/28929 A1 | 4/2002 |
| WO | WO 03/074026 A1 | 9/2003 |
| WO | WO 03/074090 A2 | 9/2003 |

OTHER PUBLICATIONS

V. Bütün et al., "Synthesis and aqueous solution properties of near-monodisperse tertiary amine methacrylate homopolymers and diblock copolymers", *Polymer*, vol. 42, 2001, pp. 5993-6008.
K.L. Robinson et al., "Controlled Polymerization of 2-Hydroxyethyl Methacrylate by ATRP at Ambient Temperature", *Macromolecules*, vol. 34, 2001, pp. 3155-3158.
J.H. Laurer et al., "Morphology and Rheology of SIS and SEPS Triblock Copolymers in the Presence of a Midblock-Selective Solvent", *Langmuir*, vol. 15, 1999, pp. 7947-7955.
Ga-Er Yu et al., "Micellisation and Gelation of Triblock Copoly(oxyethylene/oxy-propylene/oxyethylene), F127", *J. Chem. Soc. Faraday Trans.*, vol. 17, 1992, pp. 2537-2544.
J.H. Truelsen et al., "Block Copolymers with pH-Responsive Poly(sodium 4-vinylbenzoates) Synthesized by Atom Transfer Radical Polymerization", *ACS Polymer Preprint*, vol. 43, No. 2, 2002, pp. 257-258.

* cited by examiner

*Primary Examiner*—Robert D. Harlan
(74) *Attorney, Agent, or Firm*—Sughrue Mion, PLLC

(57) ABSTRACT

Block copolymers comprise a core block formed of hydrophilic monomers and have pendant zwitterionic groups, and at least two terminal blocks, comprising stimulus-responsive groups. The core block has a degree of polymerisation of at least 100, whilst the terminal blocks have an average degree of polymerisation of at least 20. A solution of polymer in a liquid may be caused to change its characteristics, for instance rheology, upon being subjected to a stimulus such as a change in temperature or pH. Examples comprise core blocks formed of 2-methacryloyloxyethyl-2'-trimethylammonium ethylphosphate inner salt (MPC) and terminal blocks formed of 2-(diisopropylamino)ethyl methacrylate. Upon changing the pH from around 2 to around 8, an aqueous solution of the block copolymer gels, the solution becoming mobile again upon lowering the pH. The effect is due to deprotonation of a quaternary ammonium pendant ion to form a non-ionised group and subsequent protonation to form an ionised group. This changes the hydrophilicity of the terminal blocks and allowing formation of a network of micellar structures when the pendant groups are not ionised and relatively hydrophobic and associated in micelles.

35 Claims, 10 Drawing Sheets

Set-up for *in situ* UV Measurement of Drug Release

Drug Release from Triblock Copolymer Gels

Conditions: 15 % copolymer solution with 5 % dipyridamole based on copolymer. The total drug concentration in the final gel is 0.6 %.

Slow, sustained drug release is achieved from the triblock copolymer gel!

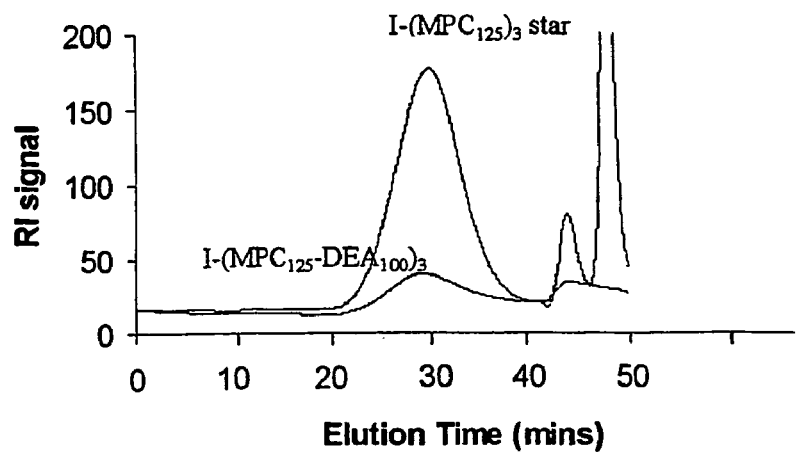
Figure 14
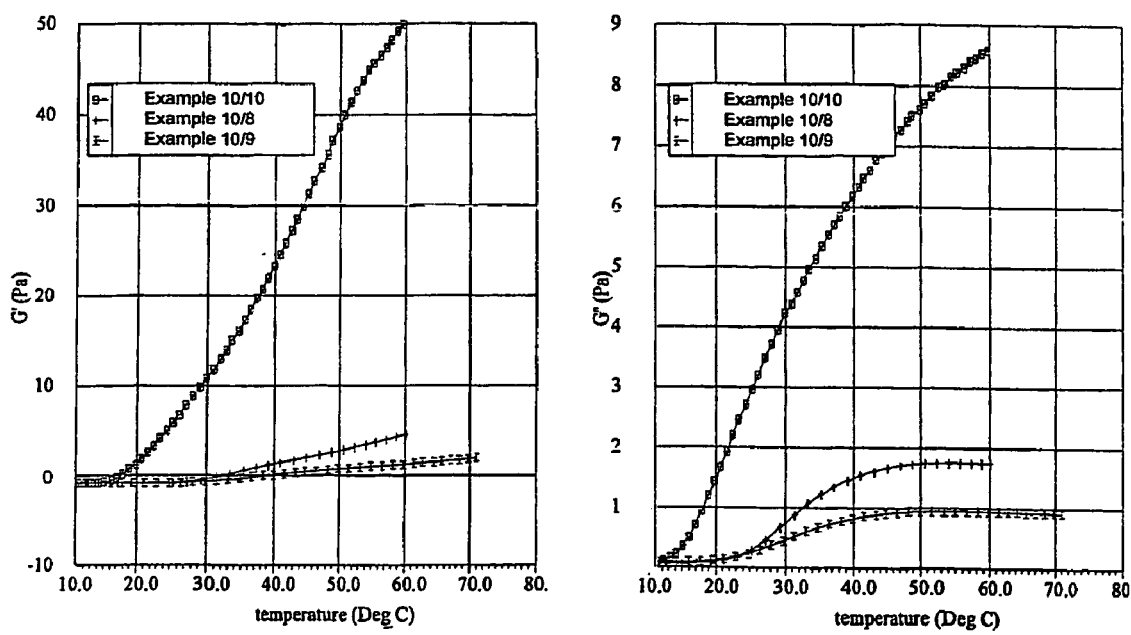
Figure 15: Rheological properties of three-arm star thermo-responsive gels

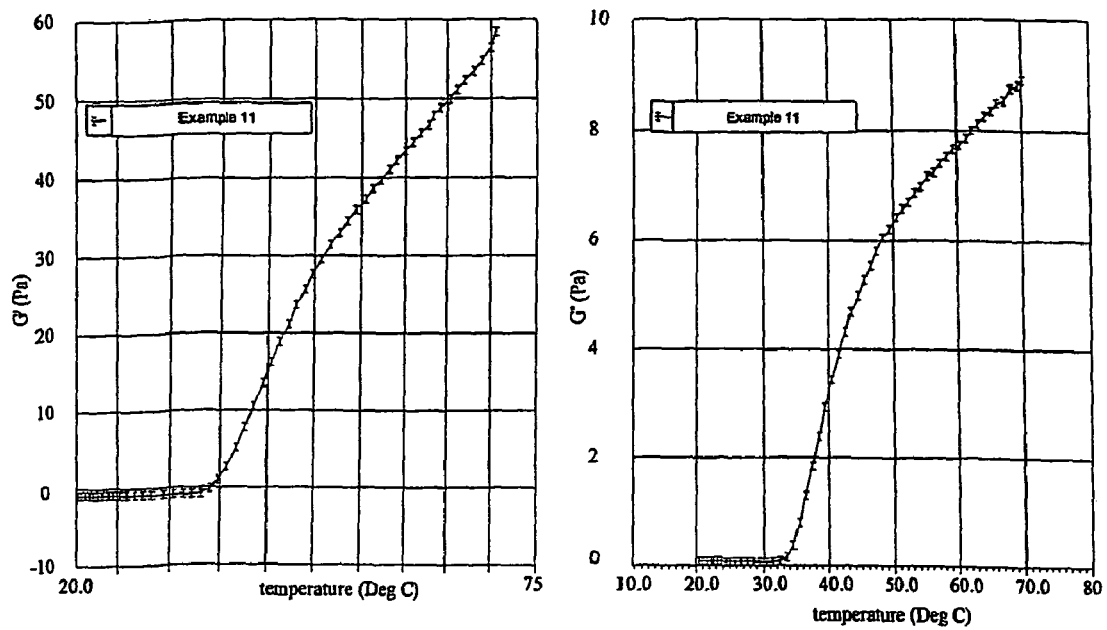
Figure 16: Rheological properties of three-arm star NIPAM-based thermo-responsive gel Example 11.

BLOCK COPOLYMERS

The present invention relates to block copolymers which have the ability to undergo changes, when exposed to selected stimuli, often reversibly. For instance, aqueous solutions of the block copolymers may be gelled by changing the pH of the environment, and may be used as drug delivery systems.

We have previously reported controlled radical polymerisation, using atom transfer radical polymerisation (ATRP) processes, to polymerise 2-methacryloyloxyethyl-trimethylammoniumethyl phosphate inner salt (MPC), in WO-A-0228929. The technique allows control of the molecular weight of the polymer and is particularly useful for forming block copolymers by sequential monomer addition. Block copolymers were formed inter alia with 2-hydroxyethylmethacrylate (HEMA), dimethylamino ethyl methacrylate methyl chloride salt (DMAEMA.MeCl), poly(propylene glycol), sodium 4-styrene sulphonate, carboxybetaine ethyl methacrylate, methylmethacrylate, 2-(dimethylamino) ethyl methacrylate (DNA) and 2-(diethylamino) ethyl methacrylate (DEA). Triblock copolymers were also formed, by a three step process. In none of the examples was a block copolymer formed having a core block comprising MPC and more than one terminal block extending therefrom formed of a stimulus responsive monomer. A block copolymer (A-B) of MPC with DEA was shown to form micelles by adjustment of the pH of an aqueous solution, in particular by raising the pH from 1.37 to 8.68.

In WO-A-03074026, not published at the priority date, we describe amphiphilic block copolymers having hydrophilic block, usually formed of MPC, and a relatively hydrophobic block. The relatively hydrophobic block comprised diethylamino ethyl methacrylate. These A-B type block copolymers were pH sensitive, whereby micelles could be formed at high pH, whereby hydrophobic actives partitioned into the hydrophobic micelle cores. Although it was suggested that the block copolymers could be A-B-A or B-A-B copolymers, there were no worked examples on such polymers. The properties of such copolymers were not predicted.

Truelsen, J. H. et al in ACS Polymer Preprints, 2002, 43 (2), 257-258, describe A-B-A block copolymers which are pH responsive. The B block is formed of poly(ethylene oxide), whilst the A blocks are formed of poly (sodium 4-vinylbenzoate). The polymers showed a pH-dependent behaviour, such that at pH's above the pKa of poly(4-vinylbenzoic acid) (about 4.4) the block copolymer formed a mobile solution and at pH's below the pKa the block copolymer micellised at low concentrations and formed a gel at high concentrations. The acidic groups at low pH are protonated and the A blocks consequently hydrophobic such that they are associated with one another.

U.S. Pat. No. 5,441,841 describes A-B block copolymers. One block may have pendant zwitterionic groups.

One of the problems which may be solved by the present inventions is the provision of block copolymers which are capable of gelling in aqueous solution under conditions which are relatively mild, for instance at around neutral pH or at body temperature.

According to the present invention there is provided a new composition comprising a solvent and a block copolymer, which block copolymer comprises a hydrophilic core block and at least two terminal blocks, each terminal block being stimulus-responsive in which the blocks are each formed at least in part by the polymerisation of ethylenically unsaturated monomers, wherein the average degree of each terminal block is at least 20 characterised in that the core block comprises zwitterionic pendant groups, and has a degree of polymerisation of at least 100.

The block copolymer used in the invention may comprise a core with more than 2, for instance 3 or more, terminal groups attached, for instance having a star architecture. Alternatively the core block may be the backbone of a comb type polymer, having multiple pendant blocks each forming terminal groups. Very useful block copolymers are simple A-B-A triblock copolymers, generally in which each of the A blocks is identical, and form in the same polymerisation step.

Preferably the monomers from which the core block is formed comprise compounds of the general formula I $$YBX \qquad \qquad I$$

in which Y is an ethylenically unsaturated group selected from $H_2C=CR-CO-A-$, $H_2C=CR-C_6H_4-A^1-$, $H_2C=CR-CH_2A^2$, $R^2O-CO-CR=CR-CO-O$, $RCH=CH-CO-O-$, $RCH=C(COOR^2)CH_2-CO-O$,

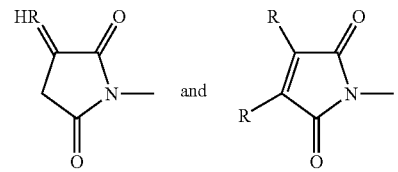

and

A is $-O-$ or $NR^1$;
A$^1$ is selected from a bond, $(CH_2)_lA^2$ and $(CH_2)_lSO_3-$ in which l is 1 to 12;
A$^2$ is selected from a bond, $-O-$, $O-CO-$, $CO-O$, $CO-NR^1-$, $-NR^1-CO$, $O-CO-NR^1-$, $NR^1-CO-O-$;
R is hydrogen or $C_{1-4}$ alkyl;
R$^1$ is hydrogen, $C_{1-4}$ alkyl or BX;
R$^2$ is hydrogen or $C_{1-4}$ alkyl;
B is a bond, or a straight branched alkanediyl, alkylene oxaalkylene, or alkylene (oligooxalkylene) group, optionally containing one or more fluorine substituents;
X is a zwitterionic group.

Preferably X is an ammonium, phosphonium, or sulphonium phosphate or phosphonate ester zwitterionic group, more preferably a group of the general formula II

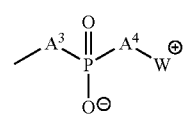

in which the moieties A$^3$ and A$^4$, which are the same or different, are $-O-$, $-S-$, $-NH-$ or a valence bond, preferably $-O-$, and W$^+$ is a group comprising an ammonium, phosphonium or sulphonium cationic group and a group linking the anionic and cationic moieties which is preferably a $C_{1-12}$-alkanediyl group, preferably in which W$^+$ is a group of formula $$-W^1-N^+R^3{}_3, -W^1-P^+R^4{}_3, -W^1-S^+R^4{}_2 \text{ or}$$
$$-W^1\text{-Het}^+ \text{ in which:}$$

W$^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus- or sulphur-, preferably nitrogen-, containing ring, for example pyridine.

Monomers in which X is of the general formula in which $W^+$ is $W^1N^{\ominus}R^3{}_3$ may be made as described in our earlier specification WO-A-9301221. Phosphonium and sulphonium analogues are described in WO-A-9520407 and WO-A-9416749.

Generally a group of the formula II has the preferred general formula III

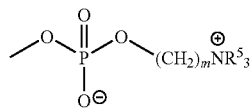

III where the groups $R^5$ are the same or different and each is hydrogen or $C_{1-4}$ alkyl, and m is from 1 to 4, in which preferably the groups $R^5$ are the same preferably methyl.

In phosphobetaine based groups, X may have the general formula IV

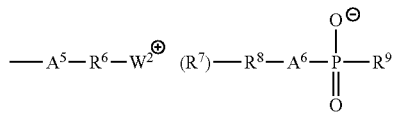

IV in which $A^5$ is a valence bond, —O—, —S— or —NH—, preferably —O—;

$R^6$ is a valence bond (together with $A^5$) or alkanediyl, —C(O)alkylene- or —C(O)NH alkylene preferably alkanediyl, and preferably containing from 1 to 6 carbon atoms in the alkanediyl chain;

$W^2$ is S, $PR^7$ or $NR^7$;

the or each group $R^7$ is hydrogen or alkyl of 1 to 4 carbon atoms or the two groups $R^7$ together with the heteroatom to which they are attached form a heterocyclic ring of 5 to 7 atoms;

$R^8$ is alkanediyl of 1 to 20, preferably 1 to 10, more preferably 1 to 6 carbon atoms;

$A^6$ is a bond, NH, S or O, preferably O; and $R^9$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Monomers comprising a group of the general formula IV may be made by methods as described in JP-B-03-031718, in which an amino substituted monomer is reacted with a phospholane.

In compounds comprising a group of the general formula IV, it is preferred that $A^5$ is a bond;
$R^6$ is a $C_{2-6}$ alkanediyl;
$W^2$ is $NR^7$:
each $R^7$ is $C_{1-4}$ alkyl;
$R^8$ is $C_{2-6}$ alkanediyl;
$A^6$ is O; and
$R^9$ is $C_{1-4}$ alkoxy.

Alternatively X may be a zwitterion in which the anion comprises a sulphate, sulphonate or carboxylate group.

One example of such a group is a sulphobetaine group, of the general formula V

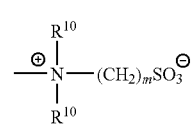

V where the groups $R^{10}$ are the same or different and each is hydrogen or $C_{1-4}$ alkyl and m is from 2 to 4.

Preferably the groups $R^{36}$ are the same. It is also preferable that at least one of the groups $R^{36}$ is methyl, and more preferable that the groups $R^{36}$ are both methyl.

Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer. Such groups may be represented by the general formula VI

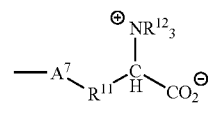

VI in which $A^7$ is a valence bond, —O—, —S— or —NH—, preferably —O—, $R^{11}$ is a valence bond (optionally together with $A^7$) or alkanediyl, —C(O)alkylene- or —C(O)NHalkylene, preferably alkanediyl and preferably containing from 1 to 6 carbon atoms; and the groups $R^{12}$ are the same or different and each is hydrogen or alkyl of 1 to 4 carbon atoms, preferably methyl, or two or three of the groups $R^{12}$, together with the nitrogen to which they are attached, form a heterocyclic ring of from 5 to 7 atoms, or the three group $R^{12}$ together with the nitrogen atom to which they are attached form a fused ring heterocyclic structure containing from 5 to 7 atoms in each ring.

Another example of a zwitterion having a carboxylate group is a carboxy betaine —$N^{\oplus}(R^{13})_2(CH_2)_rCOO^{\ominus}$ in which the $R^{13}$ groups are the same or different and each is hydrogen or $C_{1-4}$ alkyl and p is 2 to 6, preferably 2 or 3.

In the zwitterionic monomer of the general formula I it is preferred that the ethylenic unsaturated group Y is $H_2C=CR-CO-A-$. Such (alk) acrylic moieties are preferably methacrylic, that is in which R is methyl, or acrylic, in which R is hydrogen. Whilst the compounds may be (alk) acrylamido compounds, that is in which A is $NR^1$, in which case $R^1$ is preferably hydrogen, or less preferably, methyl, most preferably the compounds are esters, that is in which A is O.

In monomers of the general formula I, especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-2'-trimethylammonium ethyl phosphate inner salt.

Preferably the monomers from which the terminal blocks are formed comprise compounds of the formula VI

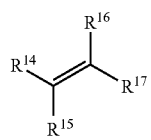

VI where $R^{14}$ is selected from the group consisting of hydrogen, halogen, $C_{1-4}$ alkyl and groups $COOR^{18}$ in which $R^{18}$ is selected from the group consisting of hydrogen and $C_{1-4}$ alkyl;

$R^{15}$ is selected from the group consisting of hydrogen, halogen and $C_4$-1 alkyl;

$R^{16}$ is selected from the group consisting of hydrogen, halogen, $C_{1-4}$ alkyl and groups $COOR^{18}$ provided that $R^{14}$ and $R^{16}$ are not both $COOR^{18}$ or $R^{14}$ and $R^{16}$ may together form $CONR^{19}CO$ in which $R^{19}$ is a $C_{1-20}$ alkyl group; and $R^{17}$ is selected from the group consisting of $C_{1-10}$alkyl, $C_{1-20}$ alkoxycarbonyl, mono- and di-($C_{1-20}$ alkyl) amino carbonyl, $C_{6-20}$ aryl, $C_{7-20}$ aralkyl, $C_{6-20}$ aryloxy carbonyl, $C_{7-20}$ aralkoxyl carbonyl, $C_{6-20}$ arylamino carbonyl, $C_{7-20}$ aralkyl amino carbonyl, $C_{2-20}$ aralkylamino and $C_{2-10}$ acyloxy groups, in which an alkyl or aryl group has a substituent which is responsive to a stimulus and in which any of the alkyl or aryl groups may additionally be substituted by one or more substituents selected from halogen atoms, alkoxy, oligo-alkoxy, aryloxy, acyloxy, acylamino, amine (including mono and di-alkyl amino and trialkylammonium in which the alkyl groups may be substituted), carboxyl, sulphonyl, phosphoryl, phosphino, (including mono- and di-alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups.

Generally the stimulus-responsive substituent is a proton donor or proton acceptor preferably one which has that property when the polymer is in an aqueous environment in the pH range 2 to 10. Terminal blocks formed from monomers having such groups generally confer pH-sensitivity on the block copolymer.

Preferably in the monomer of the general formula VI, the stimulus-responsive substituent comprises a group selected from carboxylic, carboxylate, $SO_3H$, $SO_3^-$, $PO_3HR^{20}$ and $PO_2-R^{20}$ and $PO_3^{2-}$, in which $R^{20}$ is selected from the group consisting of hydroxyl, $C_{1-12}$ alkyl $C_{1-12}$ alkoxy, $C_{6-18}$ aryl, $C_{6-18}$ aryloxy, $C_{7-18}$ aralkyl and $C_{7-18}$ aralkoxy.

In an alternative embodiment, in monomers of the general formula VI, the stimulus responsive substituent is selected from the group consisting of $NR^{21}_2$, $N^+R^{21}_2H$, $PR^{22}_2$, $P^+R^{22}_2H$, $SR^{21}$, $S^+R^{21}H$, wherein the or each group $R^{21}$ is selected from the group consisting of hydrogen, optionally substituted $C_{1-20}$ alkyl and aryl, or the two groups $R^{21}$ are joined to form, together with the heteroatom to which they are each attached, a 5-7 membered heterocycle, and each $R^{22}$ is $R^{21}$ or $OR^{21}$.

Preferably, in the monomer of the general formula VI, each of $R^{14}$ and $R^{15}$ is H, $R^{16}$ is selected from hydrogen and $C_{1-4}$ alkyl, and $R^{17}$ is a $C_{1-20}$ alkoxy carbonyl group, or a mono- or di-($C_{1-20}$ alkyl) amino carbonyl, having a substituent which is a group $NR^{21}_2$. Preferably the groups $R^{21}$ are alkyl groups and are the same as one another. Preferably an alkyl group $R^{21}$ is a branched $C_{3-6}$ alkyl group, most preferably isopropyl. Preferably $R^{17}$ is a $C_{2-12}$-alkoxy carbonyl, most preferably $C_{2-6}$ alkoxy carbonyl. Preferably $R^{16}$ is hydrogen or methyl.

Either or both the core and terminal blocks may include comonomers, for instance to provide functionality, control over hydrophobicity, control over pH sensitivity, $pK_A$ or $pK_B$ as the case may be or other stimulus responsiveness, or as general diluents. For instance comonomers providing functionality may be useful to provide conjugation of pendant groups following polymerisation to targeting moieties, or to provide for conjugation between the biologically active molecule and the polymer. Alternatively, functional groups may allow for crosslinking of the polymer following exposure to a stimulus to confer increased stability on the resultant structure. Comonomers may be selected from compounds of the general formula VII

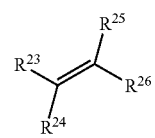

VII in which $R^{23}$ is selected from the group consisting of hydrogen, halogen, $C_{1-4}$ alkyl and groups $COOR^{27}$ in which $R^{27}$ is hydrogen and $C_{1-4}$ alkyl;

$R^{24}$ is selected from the group consisting of hydrogen, halogen and $C_{1-4}$ alkyl;

is $R^{25}$ is selected from the group consisting of hydrogen, halogen, $C_{1-4}$ alkyl and groups $COOR^{27}$ provided that $R^{23}$ and $R^{25}$ are not both $COOR^{27}$; and $R^{26}$ is selected from the group consisting of $C_{1-10}$ alkyl, $C_{1-20}$ alkoxycarbonyl, mono- and di-($C_{1-20}$ alkyl) amino carbonyl, $C_{6-20}$ aryl (including alkaryl), $C_{7-20}$ aralkyl, $C_{6-20}$ aryloxycarbonyl, $C_{7-20}$-aralkyloxycarbonyl, $C_{6-20}$ arylamino carbonyl, $C_{7-20}$ aralkyl-amino carbonyl, hydroxyl and carboxylic $C_{2-10}$ acyloxy groups, any of which may have one or more substituents selected from the group consisting of halogen atoms, alkoxy, oligo-alkoxy, aryloxy, acyloxy, acylamino, amine (including mono and di-alkyl amino and trialkylammonium in which the alkyl groups may be substituted), carboxyl, sulphonyl, phosphoryl, phosphino, (including monoand di-alkyl phosphine and tri-alkylphosphonium), zwitterionic, hydroxyl, vinyloxycarbonyl and other vinylic and allylic groups, and reactive silyl and silyloxy groups, such as trialkoxysilyl groups;

or $R^{26}$ and $R^{25}$ or $R^{25}$ and $R^{23}$ may together form —$CONR^{28}CO$ in which $R^{28}$ is a $C_{1-20}$ alkyl group.

It is preferred for at least two of the groups $R^{23}$, $R^{24}$, $R^{25}$ and $R^{26}$ to be halogen or, more preferably, hydrogen atoms. Preferably $R^{23}$ and $R^{24}$ are both hydrogen atoms. It is particularly preferred that compound of general formula VII be a styrene-based or (alk)acrylic based compound. In styrene based compounds $R^{26}$ represents an aryl group, especially a substituted aryl group in which the substituent is an amino alkyl group, a carboxylate or a sulphonate group. Where the comonomer is an (alk)acrylic type compound, $R^{26}$ is an alkoxycarbonyl, an alkyl amino carbonyl, or an aryloxy carbonyl group $R^{23}$ and $R^{24}$ are each hydrogen and $R^{25}$ is hydrogen or $C_{1-4}$ alkyl. Most preferably in such compounds $R^{26}$ is a $C_{1-20}$-alkoxy carbonyl group, optionally having a hydroxy substituent. (Alk)acrylic compounds are generally methacrylic in which case $R^{25}$ is methyl.

Preferably the comonomer is a non-ionic comonomer, such as a $C_{1-24}$ alkyl(alk)-acrylate or -acrylamide, mono- or di-hydroxy-$C_{1-6}$-alkyl(alk)-acrylate, or acrylamide, oligo($C_{2-3}$ alkoxy) $C_{2-18}$-alkyl (alk)-acrylate, or -acrylamide, styrene, vinylacetate or N-vinyllactam.

Where a comonomer is present in the respective block its amount is preferably up to 90% by mole, more preferably up to 50% by mole.

For optimum control of stimulus response, the block copolymers should have controlled molecular weights. It is preferable for each of the blocks to have a molecular weight controlled within a narrow band, that is to have a narrow polydispersity of molecular weight. The polydispersity of molecular weight of the core block should, for instance, be less than 2.0, more preferably less than about 1.5, for instance in the range 1.1 to 1.5. Similarly, the molecular weight of the terminal block should be controlled, for instance in the range 1.1 to 3.0 preferably 1.2 to 2.0.

The degree of polymerisation of the core block, in the preferred A-B-A block copolymer, is directly proportional to the distance between the two terminal blocks. The distance has an effect on the change in properties due to the imposition of the external stimulus. The degree of polymerisation is at least 100, more preferably at least 150, for instance 200 or more. It may not be necessary to have a degree of polymerisation above about 400. Where the core block is formed of two or more arms, extending from a single central group, such as the residue of a di- or higher functional initiator, the degree of polymerisation for the core block means the total number of monomer units in all arms, rather than the number per arm. For such polymers the degree of polymerisation per arm is preferably at least 20 more preferably at least 30, most preferably 50 or more.

The degree of polymerisation of each of the terminal blocks is at least 20. Preferably the degree of polymerisation is at least 40, for instance in the range 50 to 200.

Preferably the ratio of the degree of polymerisation of the core block to the average degree of polymerisation of the terminal blocks (i.e. per block) is in the range 20:1 to 1:1, preferably in the range 10:1 to 3:1.

Many of the block copolymers are new and form part of separate is aspects of the invention. Novel block copolymers may be provided in solvent or ready for dispersion in a solvent.

The block copolymers are responsive to a stimulus, that is they change their molecular form under the imposition of an external stimulus. Preferably this change is reversible, so that upon removal of the stimulus, the block copolymer reverts to its original physical form. The change may be apparent in conditions where there is no continuous liquid phase, for instance where the block copolymer is in the form of a bulk solid, optionally blended with other polymers. Generally, however, the response to the stimulus takes place in an environment involving a continuous liquid phase, in which the polymer is dispersed, as a solution or suspension. The liquid phase may comprise organic solvents, for instance blends, especially esters, alcohols, ethers, chlorinated solvents, aromatic solvents or alkanes, but is most preferably aqueous, generally consisting only of water as a liquid, but optionally containing other dissolved materials.

In the invention the stimulus preferably effects a change in rheology. The change conveniently, comprises increase in viscosity, for instance the formation of a gel.

Stimuli to which the polymer responds may include temperature changes which effect a change in the extent to which the terminal blocks associate with one another. Thus where the terminal blocks tend to associate with one another only above, or alternatively below, a transition temperature in the solvent environment a temperature change may be used to effect the response. Suitable terminal blocks may be formed from alkyl(alk)acrylamides, such as N-isopropylacrylamide, hydroxyalkyl(alk) acrylates and dialkylaminoalkyl(alk)acrylates.

The stimulus may additionally or alternatively be a change in the concentration of dissolved ions, imposition of shear or irradiation with light or other electromagnetic radiation. Where the stimulus is a change in salt is concentration, for instance, the terminal blocks may be formed from a monomer known to confer salt-sensitivity on polymers, for instance comprising a N-morpholino group such as 2-(N-morpholino) ethyl methacrylate. Where the stimulus is a temperature change, monomers for forming the terminal block may have relatively high hydrophobicities at raised temperatures, for instance comprising hydroxy alkyl groups. Temperature sensitive changes from room temperature to body temperature are of particular value.

In one preferred embodiment, the block copolymer is responsive to a change in pH. The change in pH generally ionises or deionises the pendant groups of the terminal groups, by protonating or deprotonating them. For instance, tertiary amine groups will be protonated at low pH's under acidic conditions, and will be sufficiently hydrophilic for associating with water molecules forming molecularly dispersed solutions in aqueous liquids. When the pH is raised, to basic values, for instance above 8, the ammonium salts will be deprotonated, forming tertiary amine groups which are relatively hydrophobic, especially where the alkyl groups are propyl or higher, and especially where they are secondary alkyl groups, these pendant groups are relatively hydrophobic and prefer to form hydrophobic interactions with other like terminal groups.

Since the block copolymers have at least two terminal blocks, spaced apart by the group, they may become part of two different hydrophobically associated micelles. This allows a network of micelles through the continuous phase, forming a gel structure. This is illustrated schematically in FIG. 1 of the accompanying drawings where the stimulus is the preferred pH change. This shows schematically, in the centre, a molecularly dissolved block copolymer formed of 2-(diisopropylamino)ethyl methacrylate (DPA) terminal blocks and a core MPC block at pH 2, at which the DPA pendant groups are protonated and thus cationic. To the right is shown the effect of increasing the pH with the polymer at a relatively high concentration. A network is formed of micelles of the relatively hydrophobic, deprotonated terminal blocks, bridged by core blocks dispersed in the aqueous mixture. At lower polymer concentrations, shown to the left, where the pH is raised to deprotonate the amine groups; the terminal blocks of a single molecule are more likely to associate with one another than with the terminal blocks of other molecules, thereby forming individually dispersed micelles with the terminal blocks in the inner portion and the hydrophilic core blocks on the exterior surface, without substantial network formation.

The core block may comprise additional moieties, either as pendant groups or in the backbone. For instance poly(alkylene oxide) moieties may be present in the backbone, as a result of the use of difunctional initiators. Such difunctional initiators are used to form simultaneously two part core blocks of zwitterion-containing ethylenic monomers. It is preferable to select initiators, the residue of which will have an appropriate hydrophilicity for forming part of the hydrophilic core. Suitable initiators are based on poly(ethylene oxide), or dihalogenated dicarboxylic acid esters, such as 2,5-dibromoadipate diesters.

It may be possible to synthesise the block copolymer by initial formation of a low polydispersity, low molecular weight initial block i.e. the core block using control of initiator and chain transfer agent (which permanently terminates chain formation), with the core block then being derivatised to act as a suitable radical initiator in a subsequent terminal block forming step. Preferably, however, the polymerisation of each of the blocks is by controlled radical polymerisation for instance a living radical polymerisation process, with the core block being formed in a first step and the terminal blocks being formed together in a second step.

A living radical polymerisation process may be a group transfer radical polymerisation, for instance in which an N—O, or other carbon-, sulphur-, and oxygen-centered radical group is transferred from an initiator compound to a monomer. The process may be a radical addition fragmentation transfer (RAFT) process. Preferably, however, the process is an atom transfer radical polymerisation process. Preferably such a process is used to form each block of the block copolymer. Preferably the terminal blocks are formed simultaneously. Thus the core block should have an initiator site for each terminal block. Alternatively it may be possible to form a first terminal block in a first step, the core block in a second step and the second terminal block in a third step, but this is less preferred.

In the atom or group transfer radical polymerisation process, the initiator has a radically transferable atom or group, and the catalyst comprises a transition metal compound and a ligand, in which the transition metal compound is capable of participating in a redox cycle with the initiator and dormant polymer chain, and the ligand is either any N-, O-, P- or S-containing compound which can coordinate with the transition metal atom in a σ-bond, or any carbon-containing compound which can coordinate with the transition metal in a π-bond, such that direct bonds between the transition metal and growing polymer radicals and not formed.

Preferably the radical initiator is of the general formula VIII $$R^{29}R^{30}R^{31}C—X^2 \qquad \text{VIII}$$

where:

$X^2$ is selected from the group consisting of Cl, Br, I, $OR^{32}$, $SR^{33}$, $SeR^{33}$, $OP(=O)R^{33}$, $OP(=O)(OR^{33})_2$, O—N$(R^{33})_2$ and S—C(=S)N$(R^{33})_2$, where $R^{32}$ is alkyl of from 1 to 20 carbon atoms in which each of the hydrogen atoms may be independently replaced by halide, $R^{33}$ is aryl or a straight or branched $C_1$-$C_{20}$ alkyl group, and where an N$(R^{33})_2$ group is present, the two $R^{33}$ groups may be joined to form a 5- or 6-membered heterocyclic ring; and $R^{29}$, $R^{30}$ and $R^{31}$ are each independently selected from the group consisting of H, halogen, $C_1$-$C_{20}$ alkyl, $C_3$-$C_8$ cycloalkyl, C(=O)$R^{34}$, C(=O)N$R^{35}R^{36}$, COCl, OH, CN, $C_2$-$C_{20}$ alkenyl, $C_2$-$C_{20}$ alkenyl oxiranyl, glycidyl, aryl, heterocyclyl, aralkyl, aralkenyl, $C_1$-$C_6$ alkyl in which from 1 to all of the hydrogen atoms are replaced with halogen, and $C_1$-$C_6$ alkyl substituted with from 1 to 3 substituents selected from the group consisting of $C_1$-$C_4$ alkoxy, aryl, heterocyclyl, C(=O)$R^{34}$, C(=O)N$R^{35}R^{36}$, —C$R^{30}R^{31}X^2$, $X^2R^{31}R^{30}$C-alkoxy $X^2R^{31}R^{30}$C-oligo(alkoxy) oxiranyl and glycidyl;

where $R^{34}$ is alkyl of from 1 to 20 carbon atoms, alkoxy of from 1 to 20 carbon atoms, oligo(alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, alkoxycarbonyl, alkenoxycarbonyl, aryl and hydroxy) and hydroxyl groups; and $R^{35}$ and $R^{36}$ are independently H or alkyl of from 1 to 20 carbon atoms which alkyl groups, in turn may have substituents selected from acyl, alkoxycarbonyl, alkenoxycarbonyl, aryl and hydroxy, or $R^{35}$ and $R^{36}$ may be joined together to form an alkanediyl group of from 2 to 5 carbon atoms, thus forming a 3- to 6-membered ring;

such that not more than two of $R^{29}$, $R^{30}$ and $R^{31}$ are H.

In the initiator of the general formula VII it is preferred that no more than one of $R^{29}$, $R^{30}$ and $R^{31}$, and preferably none, is hydrogen. Suitably at least one, and preferably both of $R^{29}$ and $R^{30}$ is methyl. $R^{31}$ is suitably a group CO—$R^{34}$ in which $R^{35}$ is preferably alkoxy of from 1 to 20 carbon atoms, oligo (alkoxy) in which each alkoxy group has 1 to 3 carbon atoms, aryloxy or heterocyclyloxy any of which groups may have substituents selected from optionally substituted alkoxy, oligoalkoxy, amino (including mono- and di-(alkyl) amino and trialkyl ammonium, which alkyl groups, in turn may have substituents selected from acyl, alkoxycarbonyl, alkenoxycarbonyl, aryl and hydroxy) acyloxy, acylamino, and hydroxyl groups substituents in an alkoxy group or in alkyl group which is substituted non amine substituent may include an acyloxy substituent which may have a substituent $CR^{29}R^{30}X^2$.

Since any of $R^{29}$, $R^{30}$ and $R^{31}$ may comprise a substituent $C^{30}R^{31}X^2$, the initiator may be di-, oligo- or poly-functional. Where the terminal blocks are formed simultaneously by ATRP this is preferred since the use of di- or higher-functional initiators for the core block produces initiator moieties at each of the growing ends. Terminal blocks may be formed by initiation at each such moiety. The core block will contain a residue of the initiator compound. For instance, preferably $R^{29}$ and optionally also $R^{30}$ is a $C_{1-6}$ alkyl substituted with $CR^{30}R^{31}X^2$, $X^2R^{31}R^{30}$—C—$C_{1-4}$ 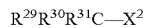 alkoxy- and $X^2R^{31}R^{30}$C— oligo ($C_{1-4}$ alkoxy). For instance the initiator may have the general formula XI

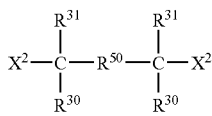

(IX)

wherein $R^{50}$ is a $C_{2-6}$ alkanediyl, preferably straight chain, or an oligo ($C_{2-3}$ alkoxy)-$C_{2-3}$ alkyl;

$X^2$ is a halide;

each $R^{31}$ is selected from the groups listed for formula VIII above and is preferably hydrogen; and each $R^{30}$ is selected from the groups listed for formula VIII above and is preferably a group $COR^{34}$ in which $R^{34}$ is selected from the groups listed for formula VIII above and is preferably a $C^{1-6}$ alkoxy group.

Block copolymers formed from tri-functional initiators are novel and have particularly useful properties.

Selection of a suitable initiator is based on various considerations. Where the polymerisation is carried out in the liquid phase, in which the monomers are dissolved, it is preferable for the initiator to be soluble in that liquid phase. The initiator is thus selected for its solubility characteristics according to the solvent system which in turn is selected according to the monomers being polymerised. Since the monomers from which the core block is formed are hydrophilic it is convenient to polymerise them in water or a lower alkanol. The initiator should thus be water-soluble or alcohol-soluble. Water-soluble initiators include, for instance the reaction product of dihydroxy-capped oligo(ethylene oxide) with 2-bromoisobutyryl bromide. An example of an alcohol soluble initiator is diethylmeso-2,5-bromodipate.

The portion of the initiator $—C—R^{29}R^{30}R^{31}$ becomes joined to the first monomer of the growing polymer chain. Where the initiator has the formula IX above, the moiety $R^{50}(CR^{30}R^{31})_2^-$ becomes incorporated between two sub-blocks of which the core block is comprised.

New block copolymers having a star type architecture may be made from, for instance, tri- or higher-functional initiators, such as based on sugar compounds. Such initiators may be used to form the initial core block as several branches, each one of which has a terminal block polymerised thereon. By the use of star type copolymers, even more extensive networks may be formed to give improved control over the stimulus-imposed changes.

A comb-type polymer may be formed by a process in which the core block is formed as a polymer with low polydispersity from monomers including functional pendant groups (such as amino or hydroxyl-containing groups) which can be converted to initiator sites for the step of forming terminal blocks using an atom or group radical transfer polymerisation technique. Alternatively macro initiator for atom or group transfer polymerisation, which is a polymer with multiple pendant initiator sites, may be used in a first core block forming step, in which branches of core block are formed at each site, with terminal blocks being formed on each branch in a second step, whereby a graft-type polymer is formed. The group $X^2$ becomes joined to the end units of the polymer chain in the core block forming step and then in the terminal block forming step.

In an atom or group radical transfer polymerisation process the transition metal compound which comprises a component of the catalyst is $M_t^{q+}X^3_q$, where:

$M_t^{q+}$ may be selected from the group consisting of $Cu^{1+}$, $Cu^{2+}$, $Fe^{2+}$, $Fe^{3+}$, $Ru^{2+}$, $Ru^{3+}$, $Cr^{2+}$, $Cr^{3+}$, $Mo^{2+}$, $Mo^{3+}$, $W^{2+}$, $W^{3+}$, $Mn^{2+}$, $Mn^{3+}$, $Mn^{4+}$, $Rh^{3+}$, $Rh^{4+}$, $Re^{2+}$, $Re^{3+}$, $Co^+$, $Co^{2+}$, $Co^{3+}$, $V^{2+}$, $V^{3+}$, $Zn^+$, $Zn^{2+}$, $Ni^{2+}$, $Ni^{3+}$, $Au^+$, $Au^{2+}$, $Ag^+$, and $Ag^{2+}$;

$X^3$ is selected from the group consisting of halogen, $C_1$-$C_6$-alkoxy, $(SO_4)_{1/2}$, $(PO_4)_{1/3}$, $(R^{37}PO_4)_{1/2}$, $(R^{37}_2PO_4)$, triflate, hexafluorophosphate, methanesulphonate, arylsulphonate, CN and $R^{38}CO_2$, where $R^{37}$ is aryl or a straight or branched $C_{1-20}$ alkyl and $R^{38}$ is H or a straight or branched $C_1$-$C_6$ alkyl group which may be substituted from 1 to 5 times with a halogen; and q is the formal charge on the metal ($0 \leq q \leq 7$).

Preferably $X^3$ is halide, most preferably chloride or bromide. Particularly suitable transition metal compounds are based on copper or ruthenium, for instance CuBr, CuCl or $RuCl_2$.

In the catalyst, the ligand is preferably selected from the group consisting of:

a) compounds of the formulas:

$R^{39}—Z—R^{40}$ and $R^{39}—Z—(R^{41}—Z)_m—R^{40}$ where:

$R^{39}$ and $R^{40}$ are independently selected from the group consisting of H, $C_1$-$C_{20}$ alkyl, aryl, heterocyclyl and $C_1$-$C_6$ alkoxy, $C_1$-$C_4$ dialkylamino, $C(=O)R^{42}$, $C(=O)NR^{43}_2$ and $A^7C(=O)R^{44}$, where $A^7$ may be $NR^{45}$ or O; $R^{42}$ is alkyl of from 1 to 20 carbon atoms, aryloxy or heterocyclyloxy; $R^{43}$ is independently H or alkyl of from 1 to 20 carbon atoms or the two groups $R^{43}$ may be joined together to form an alkanediyl group of from 2 to 5 carbon atoms, thus forming a 3- to 6-membered ring; $R^{44}$ is H, straight or branched $C_1$-$C_{20}$ alkyl or aryl and $R^{45}$ is hydrogen, straight or branched $C_{1-20}$-alkyl or aryl; or $R^{39}$ and $R^{40}$ may be joined to form, together with Z, a saturated or unsaturated ring;

Z is O, S, $NR^{46}$ or $PR^{46}$, where $R^{46}$ is selected from the same group as $R^{39}$ and $R^{40}$, and where Z is $PR^{46}$, $R^{46}$ can also $C_1$-$C_{20}$ alkoxy or Z may be a bond, $CH_2$ or a fused ring, where one or both of $R^{39}$ and $R^{40}$ is heterocyclyl, each $R^{41}$ is independently a divalent group selected from the group consisting of $C_1$-$C_8$ cycloalkanediyl, $C_1$-$C_8$ cycloalkenediyl, arenediyl and heterocyclylene where the covalent bonds to each Z are at vicinal positions or $R^{41}$ may be joined to one or both of $R^{39}$ and $R^{40}$ to formulate a heterocyclic ring system; and m is from 1 to 6;

b) CO;

c) porphyrins and porphycenes, which may be substituted with from 1 to 6 halogen atoms, $C_{1-6}$ alkyl groups, $C_{1-6}$-alkoxy groups, $C_{1-6}$alkoxycarbonyl, aryl groups, heterocyclyl groups, and $C_1$— alkyl groups further substituted with from 1 to 3 halogens;

d) compounds of the formula $R^{47}R^{48}C(C(=O)R^{49})_2$, where $R^{49}$ is $C_{1-20}$alkyl, $C_{1-20}$ alkoxy, aryloxy or heterocyclyloxy; and each of $R^{47}$ and $R^{48}$ is independently selected from the group consisting of H, halogen, $C_{1-20}$ alkyl, aryl and heterocyclyl, or $R^{47}$ and $R^{48}$ may be joined to form a $C_{1-8}$ cycloalkyl ring or a hydrogenated aromatic or heterocyclic ring, of which the ring atoms may be further substituted with 1 to 5 $C_{1-6}$ alkyl groups, $C_{1-6}$ alkoxy groups, halogen atoms, aryl groups, or combinations thereof; and e) arenes and cyclopentadienyl ligands, where said cyclopentadienyl ligand may be substituted with from one to five methyl groups, or may be linked through an ethylene or propylene chain to a second cyclopentadienyl ligand.

Selection of a suitable ligand is, for instance, based upon the solubility characteristics and/or the separability of the catalyst from the product polymer mixture. Generally it is preferred for catalyst to be soluble in a liquid reaction mixture, although under some circumstances it may be possible to immobilise the catalyst, for instance on a porous substrate. For the preferred process, which is carried out in the liquid phase, the ligand is soluble in a liquid phase. The ligand is generally a nitrogen containing ligand. The preferred ligand may be a compound including a pyridyl group such as bipyridine, or a pyridyl group and an imino moiety, such as

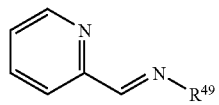

where $R^{49}$ is a suitable alkyl group, the substituent being variable and adaptable to confer desired solubility characteristics or may be triphenylphosphine or 1,1,4,7,10,10-hexamethyl-triethylene tetramine.

Such ligands are usefully used in combination with copper bromide, copper chloride and ruthenium chloride transition metal compounds as part of the catalyst.

The ratio of metal compound and ligand in the catalyst should be approximately stoichiometric, based on the ratios of the components when the metal ion is fully complexed. The ratio should preferably be in the range 1:(0.5 to 2) more preferably in the range 1:(0.8:1.25). Preferably the range is about 1:1.

In the living radical polymerisation process, the catalyst may be used in amounts such that a molar equivalent quantity as compared to the level of initiator or less is present. The ratio of catalyst (based on transition metal compound) to initiator is preferably in the range 1:(1 to 50), more preferably in the range 1:(1 to 10).

The reaction may be heterogeneous, that is comprising a solid and a liquid phase, but is more preferably homogeneous. Preferably the polymerisation is carried out in a single liquid phase. Where the monomer is liquid, it is sometimes unnecessary to include a non-polymerisable solvent. More often, however, the polymerisation takes place in the presence of a non-polymerisable solvent. The solvent should be selected having regard to the nature of the zwitterionic monomer and any comonomer, for instance for its suitability for providing a common solution containing both monomers. The solvent may comprise a single compound or a mixture of compounds. Generally it comprises a protic solvent.

It has been found that, especially where the zwitterionic monomer is MPC, that it may be desirable to include water in the polymerisation mixture. Water may be present in an amount in the range 1 to 100% by weight based on the weight of ethylenically unsaturated monomer. Preferably the total non-polymerisable solvent comprises 1 to 500% by weight based on the weight of ethylenically unsaturated monomer. It has been found that the zwitterionic monomer and water should be in contact with each other for as short a period as possible prior to contact with the initiator and catalyst. It may be desirable therefore for all the components of the polymerisation other than the zwitterionic monomer to be premixed and for the zwitterionic monomer to be added to the premix as the last additive.

The process may be carried out at raised temperature, for instance up to 60 to 100° C. However it has been found that the process proceeds sufficiently fast at ambient temperature.

The invention further provides polymerisation processes for forming the novel block copolymers.

The block copolymers of the present invention are suitable for a range of uses. They are of most value when dispersed in a liquid. The present invention further provides compositions comprising the novel block copolymers and a solvent. Preferably the solvent is aqueous, but may alternatively or additionally comprise an organic solvent as described above. The claims herein are directed to the composition prior to imposition of the stimulus and after imposition of the stimulus, that is in each of the physical forms. The composition may thus be a pourable liquid, or may be a gel i.e. having a viscoelastic properties. Gels may be pumpable, for instance upon imposition of suitable shear. Under some conditions, however, the gel should be free standing, that is it should not substantially flow in bulk form.

The zwitterionic groups, especially where these are phosphorylcholine type groups, confer useful biocompatibility on the polymer. The compositions of the invention may be useful where they are to be brought into contact with a human or animal, especially where they are to be delivered to the human or animal. The compositions are of particular utility where they are delivered in one form, for instance as a flowable liquid, and are subsequently changed by imposition of a stimulus after delivery, for instance to form a gel in situ, at a desired location within the body of a human or animal. The compositions may be of use, for instance, to deliver therapeutically or diagnostically useful agents, for instance pharmaceutically active agents, or imaging agents, for instance for diagnostic or therapeutic treatment purposes. Suitable imaging agents are for instance visible light dyes, UV dyes, radiopaque agents, nmr imaging agents and radioactive agents. The active agents may be retained in the gel, or be delivered in a controlled manner, dependent to an extent on the rheology of the composition, to adjacent tissues or the circulation.

The present invention provides block copolymers which respond and change in form upon changes in pH within a physiologically useful range.

The compositions may be subjected to the stimulus which causes the change in property whilst in contact with, for instance after delivery into, the body of a human or animal patient. The change may be a change in pH, a change in temperature, to body temperature or higher, or a change in salt concentration, for instance by contact with blood.

The invention is illustrated further in the following examples and figures, in which.

EXAMPLE 1

DPA-MPC-DPA Triblock Copolymer Example

A typical synthesis, as used for the $DPA_{50}\text{-}MPC_{250}\text{-}DPA_{50}$ triblock copolymer shown schematically below, was carried out as follows. The MPC (10.02 grams; 33.7 mmol) was polymerized in methanol at 20° C. using standard schlenk techniques with a commercially available bifunctional ATRP initiator (diethyl meso-2,5-dibromoadipate, DEDBA, obtained from Aldrich; 0.049 grams; 0.135 mmol) and a Cu(I)Br/2 bpy catalyst (0.019 g, 0.135 mmol Cu(I)Br; 0.042 g, 0.270 mmol bpy). After 4 h, the MPC conversion was typically more than 99% as judged by $^1$H NMR, and the MPC homopolymer obtained had a relatively low polydispersity (Mw/Mn=1.16 vs. poly(ethylene oxide) standards, see Table 1). Then the 2-diisopropyl-amino)ethyl methacrylate (DPA) monomer (2.89 grams; 13.5 mmol) was added to this dark brown reaction solution. After 48 h, the reaction solution was passed through a silica gel column [silica gel 60 (0.063-0.200 mm) purchased from E. Merck (Darmstadt, Germany)] to remove the spent ATRP catalyst, which resulted in the loss of around 10% copolymer due to adsorption onto the silica. After solvent evaporation, the solid copolymer was washed with excess n-hexane to remove any traces of residual DPA monomer, then freeze-dried overnight to obtain a white solid (11.6 grams).

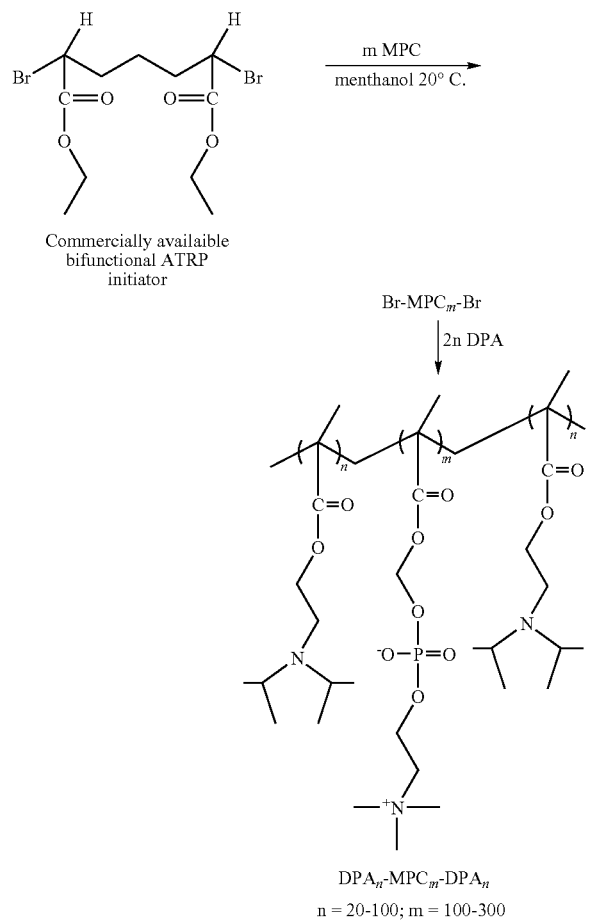

$n = 20\text{-}100; m = 100\text{-}300$

The polymer, when dissolved to form an aqueous solution at pH2 and 20%, formed a free-flowing solution. When the pH was changed to 9 the solution gelled so that, upon inversion of a sample bottle of volume approximately 20 ml, the gel did not flow.

Figure 2:
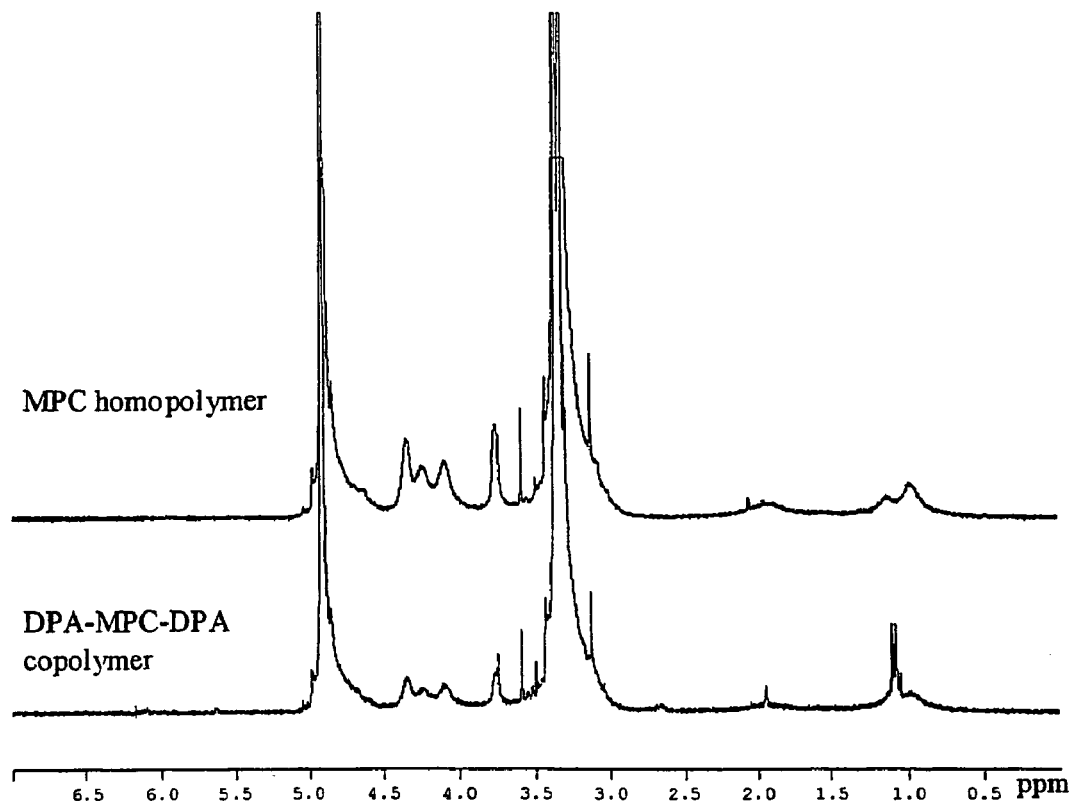
FIG. 2 shows the proton nmr spectra of one of the block copolymers formed in example 1.

FIG. 2 shows the $^1$HNMR spectra (d4-methanol) of the $DPA_{50}\text{-}MPC_{250}\text{-}DPA_{50}$ triblock copolymer. Note the absence of vinyl monomer signals at δ 5.5-6.5 and also the peak due to the DPA residues at δ 1.1 at pH9.

Figure 3:
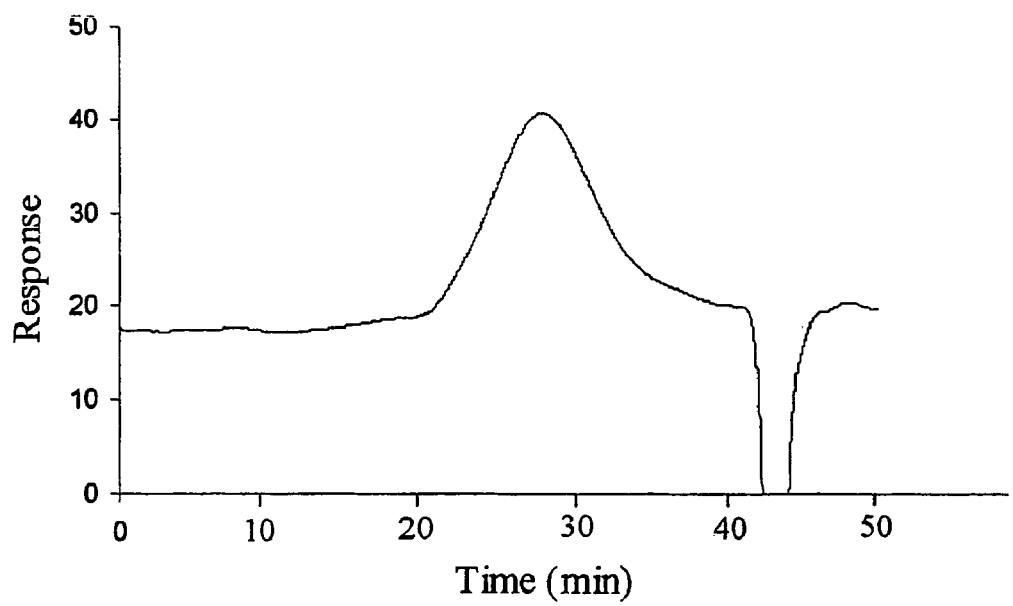
FIG. 3 shows the GPC trace of the polymer of example 1.

FIG. 3 shows the GPC trace of the $DPA_{50}\text{-}MPC_{200}\text{-}DPA_{50}$ triblock copolymer. Using the same technique block copolymers with other values of m and n in the reaction scheme are synthesised. Table 1 gives the formulation details and Table 2 gives molecular weight data of polymers.

Table 3 indicates the characteristics when aqueous solutions of polymer at pH2 are gelled by adjustment of pH to 9 at various concentrations.

Figure 4:
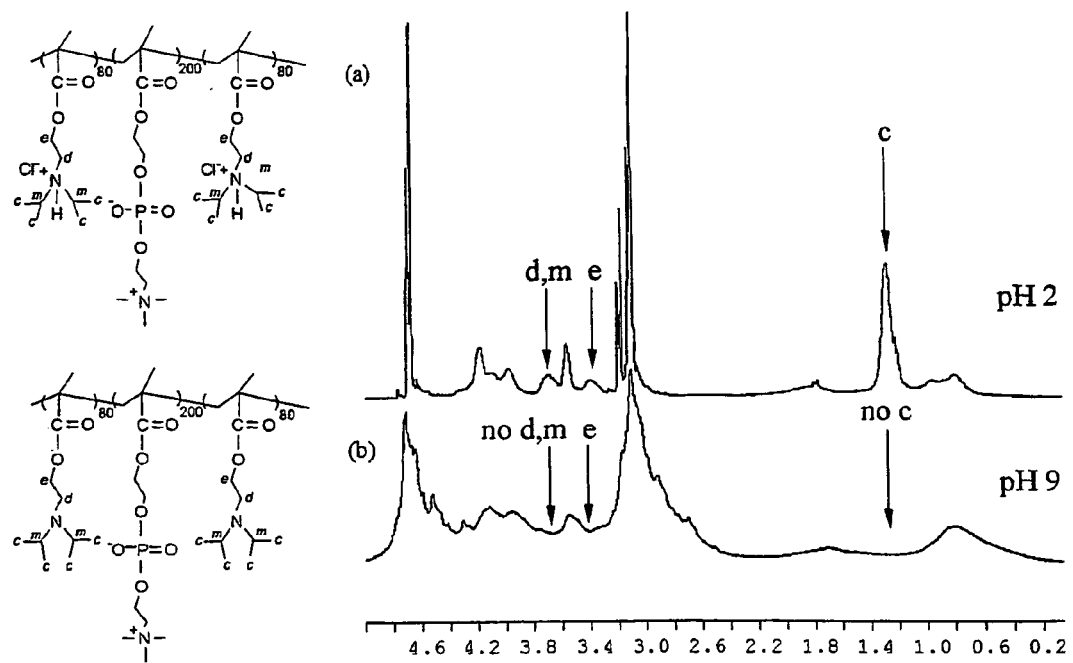
FIG. 4 shows the proton nmr spectrum for another of the block copolymers formed in example 1.
Figure 5:
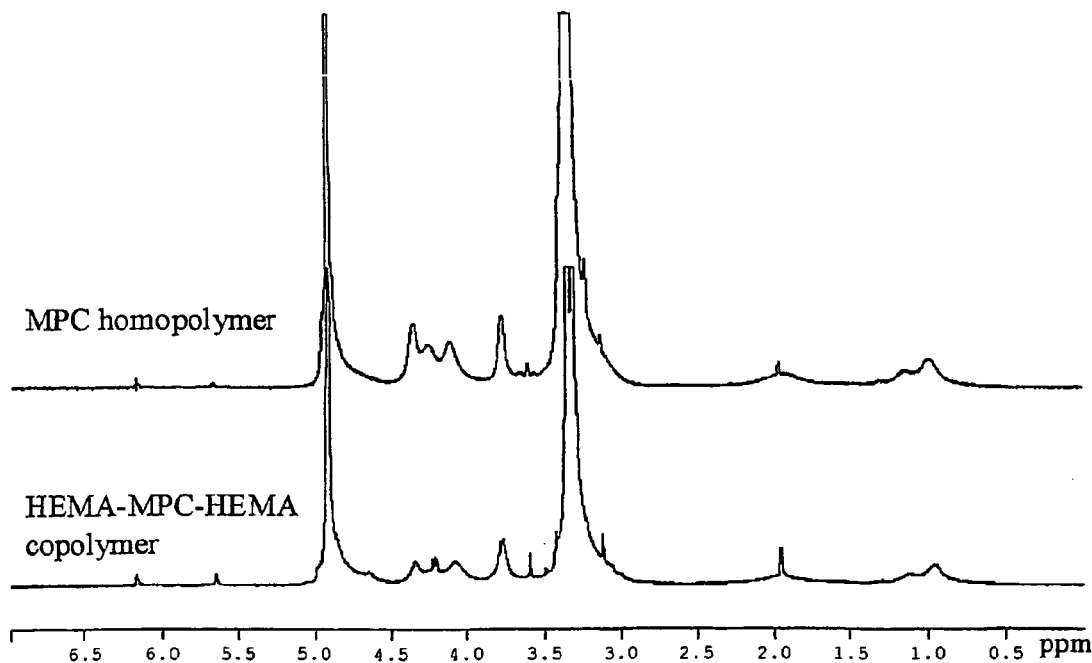
FIG. 5 shows the proton nmr spectrum of the block copolymer of example 2.
Figure 6:
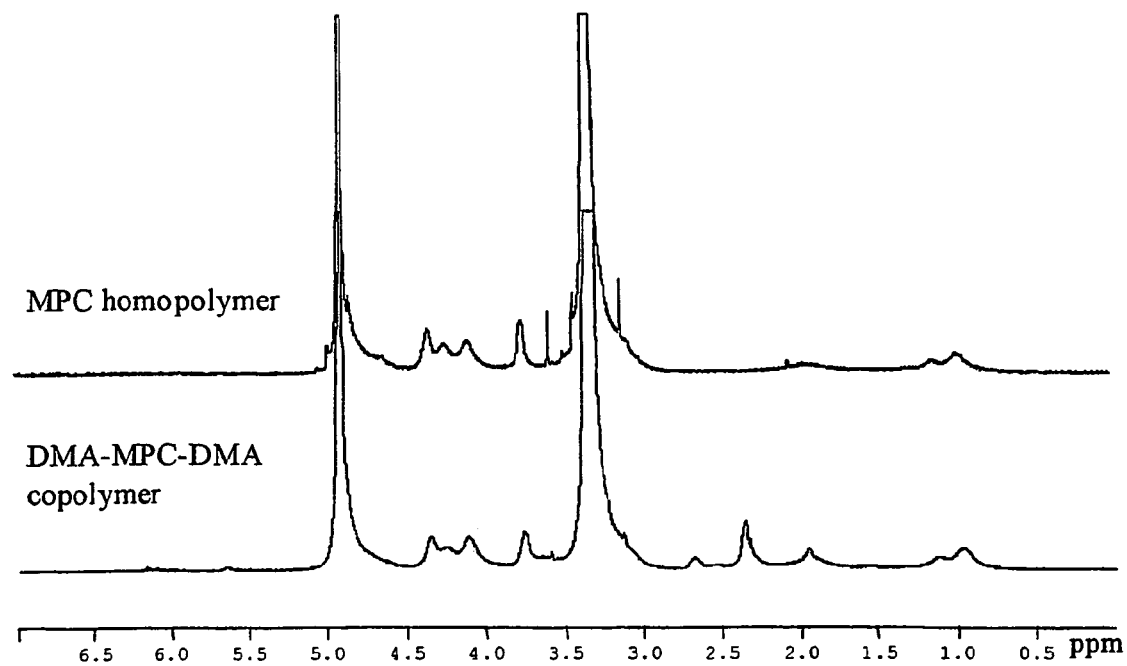
FIG. 6 shows the proton nmr spectrum of the block copolymer of example 3.
Figure 7:
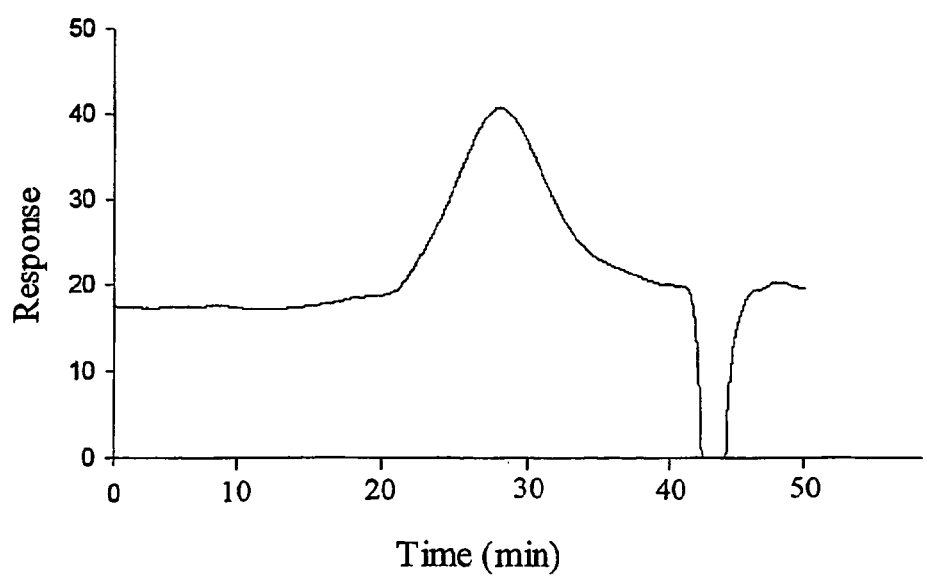
FIG. 7 shows the GPC trace of the block copolymer of example 3.

Table 4 indicates dynamic light scattering results for aqueous solutions at 0.10% w/v at the pH's indicated. FIG. 4 shows $^1$HNMR spectra obtained for the $DPA_{80}\text{-}MPC_{200}\text{-}DPA_{80}$ triblock copolymer: (a) as a free-flowing aqueous solution at pH 2 in $DCl/D_2O$ and (b) as a macroscopic physical gel at pH 9 after addition of NaOD. Note that the signals assigned to the protonated DPA residues in spectrum (a) disappear completely from spectrum (b) since the deprotonated DPA blocks become hydrophobic and hence much less solvated in the gel state.

The degree of polymerization, Dp, of each block was controlled by the initial monomer/initiator molar ratio. A summary of the various triblock compositions and molecular weight data are given in Table 1. Polydispersities of the initial MPC homopolymers prior to the addition of the DPA comonomer were typically less than 1.20, which confirms the excellent living character of this first-stage polymerization. Final triblock copolymer polydispersities ranged from 1.5 to 1.8 as judged by aqueous gel permeation chromatography (GPC), which is somewhat broader than that normally expected for ATRP syntheses (see Table 1). However, the central MPC block always had a low polydispersity, which suggests that the outer DPA blocks are quite polydisperse. Alternatively, it is possible that our aqueous GPC protocol, which involves using an acidic eluent to render the outer DPA blocks cationic, may overestimate the actual polydispersities of the triblock copolymers.

Figure 1:
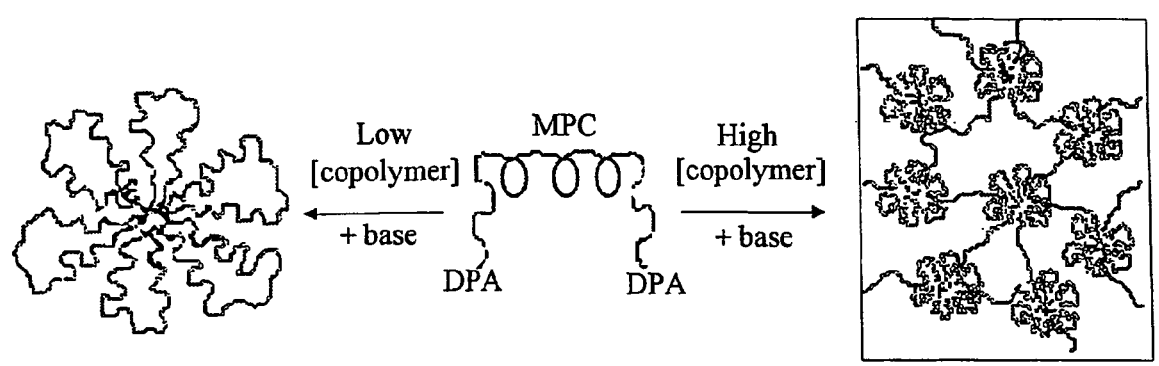
FIG. 1 is a schematic illustration of the gelation properties of the block copolymer product of example 1.

These triblock copolymers can be molecularly dissolved in acidic solution (pH<4) but on adjusting to pH 7-8 with NaOH the DPA blocks become deprotonated (the pKa of protonated DPA homopolymer is around pH 6) and hence hydrophobic, leading to attractive inter-chain interactions. So-called 'flower' micelles comprising MPC-based 'petals' and DPA cores are formed in dilute aqueous solution, see FIG. 1. For example, dynamic light scattering studies indicate an intensity-average diameter of around 68 nm for 'flower' micelles produced from a 0.10 w/v % aqueous solution of the $DPA_{50}\text{-}MPC_{250}\text{-}DPA_{50}$ triblock copolymer at pH 8. However, at higher copolymer concentrations (above 5-10 w/v %, depending on the triblock copolymer composition), macroscopic physical gels can be produced. Gelation was confirmed by simple tube inversion experiments and the results are summarized in Table 1. The phrase 'free-standing gel' is used here to describe gels that remained in position after tube inversion. The acidic solution remains fluid, whereas the neutralized solution forms a free-standing gel. Our control experiments confirmed that no such gelation occurred with the analogous MPC-DPA diblock (A-B) copolymers.

In principle, gelation will only occur at a given copolymer concentration if the central MPC-based block is sufficiently long to bridge between adjacent micelles in the aqueous milieu. Thus no gelation was is observed for a 10 w/v % solution of a $DPA_{30}$-$MPC_{100}$-$DPA_{30}$ triblock, whereas only rather soft gels were formed by a $DPA_{30}$-$MPC_{200}$-$DPA_{30}$ triblock at the same concentration (see Table 1). More robust, free-standing gels were obtained from a 10 w/v % solution of a $DPA_{50}$-$MPC_{200}$-$DPA_{50}$ triblock due to the increased hydrophobic interactions between the longer DPA chains. This gel could be dissolved molecularly on re-adjusting the solution pH to below pH 5 with HCl.

Selected DPA-MPC-DPA triblock copolymers were examined as both free-flowing solutions at low pH and as free-standing gels above pH 7 using $^1$H NMR spectroscopy. Typical spectra are depicted in FIG. 4 for a 10 w/v % aqueous solution of a $DPA_{80}$-$MPC_{200}$-$DPA_{80}$ triblock copolymer. At pH 2 all the expected NMR signals due to the central MPC block and the protonated outer DPA blocks are visible, indicating a high degree of solvation and mobility for both types of blocks under these conditions. In contrast, at pH 9 the signals due to the DPA residues are both broadened and attenuated relative to the signals for the MPC residues, indicating a significant reduction in salvation and mobility for the former blocks, which are deprotonated and hence hydrophobic at this solution pH.

TABLE 1

Formulation details for the ATRP synthesis of MPC-based triblock copolymers

| Triblock copolymer Composition | MPC g/mmol | DEDBA Initiator g/mmol | Cu(I)Br g/mmol | bpy g/mmol | DPA g/mmol |
|---|---|---|---|---|---|
| $DPA_{30}$-$MPC_{100}$-$DPA_{30}$ | 6.0/20.2 | 0.073/0.202 | 0.029/0.202 | 0.063/0.404 | 2.59/12.1 |
| $DPA_{50}$-$MPC_{100}$-$DPA_{50}$ | 6.0/20.2 | 0.073/0.202 | 0.029/0.202 | 0.063/0.404 | 4.32/20.2 |
| $DPA_{30}$-$MPC_{200}$-$DPA_{30}$ | 8.02/27.0 | 0.049/0.135 | 0.019/0.135 | 0.042/0.270 | 1.73/8.0 |
| $DPA_{50}$-$MPC_{200}$-$DPA_{50}$ | 8.02/27.0 | 0.049/0.135 | 0.019/0.135 | 0.042/0.270 | 2.89/13.5 |
| $DPA_{80}$-$MPC_{200}$-$DPA_{80}$ | 8.02/27.0 | 0.049/0.135 | 0.019/0.135 | 0.042/0.270 | 4.62/21.6 |
| $DPA_{50}$-$MPC_{250}$-$DPA_{50}$ | 10.2/33.7 | 0.049/0.135 | 0.019/0.135 | 0.042/0.270 | 2.89/13.5 |
| $DPA_{30}$-$MPC_{300}$-$DPA_{30}$ | 12.03/40.5 | 0.049/0.135 | 0.019/0.135 | 0.042/0.270 | 1.73/8.0 |
| $DPA_{50}$-$MPC_{300}$-$DPA_{50}$ | 12.03/40.5 | 0.049/0.135 | 0.019/0.135 | 0.042/0.270 | 2.89/13.5 |
| $DPA_{100}$-$MPC_{300}$-$DPA_{100}$ | 12.03/40.5 | 0.049/0.135 | 0.019/0.135 | 0.042/0.270 | 5.78/27.0 |

TABLE 2

Summary of the triblock compositions, molecular weight data of the various DPA-MPC-DPA and DMA-MPC-DMA triblock copolymers investigated in this study.

| target ABA triblock composition | Reaction time (h) homo | Reaction time (h) ABA triblock | Conversion, % homo | Conversion, % ABA triblock | Mn Homo (GPC) | Mn Triblock (GPC) | Mn ABA triblock (theory) | Mw/Mn (GPC) homo | Mw/Mn (GPC) ABA triblock | Residual Cu by ICP-AES/ ppm |
|---|---|---|---|---|---|---|---|---|---|---|
| $DPA_{30}$-$MPC_{100}$-$DPA_{30}$ | 3.5 | 20 | >99 | >99 | 29,000 | 49,000 | 43,000 | 1.12 | 1.51 | <0.3 |
| $DPA_{50}$-$MPC_{100}$-$DPA_{50}$ | 3.5 | 24 | >99 | >99 | 29,000 | 61,000 | 51,000 | 1.10 | 1.54 | <0.3 |
| $DPA_{30}$-$MPC_{200}$-$DPA_{30}$ | 4.0 | 24 | >98 | >99 | 56,000 | 105,000 | 72,000 | 1.14 | 1.61 | 2.2 |
| $DPA_{50}$-$MPC_{200}$-$DPA_{50}$ | 4.0 | 30 | >98 | >98 | 55,000 | 129,000 | 81,000 | 1.14 | 1.68 | 0.7 |
| $DPA_{80}$-$MPC_{200}$-$DPA_{80}$ | 4.0 | 36 | >98 | >98 | 56,000 | 131,000 | 94,000 | 1.16 | 1.70 | <0.3 |
| $DPA_{50}$-$MPC_{250}$-$DPA_{50}$ | 4.5 | 36 | >98 | >98 | 68,000 | 130,000 | 96,000 | 1.16 | 1.63 | 0.6 |
| $DPA_{30}$-$MPC_{300}$-$DPA_{30}$ | 5.0 | 30 | >96 | >98 | 82,000 | 136,000 | 102,000 | 1.18 | 1.72 | 1.0 |
| $DPA_{50}$-$MPC_{300}$-$DPA_{50}$ | 5.0 | 36 | >96 | >98 | 82,000 | 149,000 | 111,000 | 1.16 | 1.79 | 0.6 |
| $DPA_{100}$-$MPC_{300}$-$DPA_{100}$ | 5.0 | 48 | >96 | >97 | 82,000 | 166,000 | 132,000 | 1.20 | 1.80 | 1.2 |

TABLE 3

Summary of the gelation behavior of the various DPA-MPC-DPA triblock copolymers investigated in this study

| Target ABA triblock copolymer composition | gelation behaviour at a given copolymer concentration 5% | 10% | 15% | 20% |
|---|---|---|---|---|
| $DPA_{30}$-$MPC_{100}$-$DPA_{30}$ | No | No | No | No |
| $DPA_{50}$-$MPC_{100}$-$DPA_{50}$ | No | No | No | No |
| $DPA_{30}$-$MPC_{200}$-$DPA_{30}$ | weak gel | soft gel | free-standing gel | free-standing gel |
| $DPA_{50}$-$MPC_{200}$-$DPA_{50}$ | weak gel | soft gel | free-standing gel | free-standing gel |
| $DPA_{80}$-$MPC_{200}$-$DPA_{80}$ | soft gel | gel | free-standing gel | free-standing gel |
| $DPA_{50}$-$MPC_{250}$-$DPA_{50}$ | gel | free-standing gel | free-standing gel | free-standing gel |
| $DPA_{30}$-$MPC_{300}$-$DPA_{30}$ | weak gel | soft gel | gel | free-standing gel |
| $DPA_{50}$-$MPC_{300}$-$DPA_{50}$ | soft gel | gel | free-standing gel | free-standing gel |
| $DPA_{100}$-$MPC_{300}$-$DPA_{100}$ | gel | free-standing gel | free-standing gel | free-standing gel |

TABLE 4

Summary of the DLS data for DPA-MPC-DPA triblock copolymers investigated in this study. The triblock copolymer concentration was 0.10 w/v % in all cases

| polymer | pH | D (nm) | Polydispersity | Intensity (kcps) |
|---|---|---|---|---|
| $DPA_{30}$-$MPC_{200}$-$DPA_{30}$ | 1.90 | 17.8 | 0.33 | 5.0 |
|  | 9.56 | 37.2 | 0.06 | 40.1 |
| $DPA_{50}$-$MPC_{200}$-$DPA_{50}$ | 1.92 | 15.7 | 0.37 | 5.2 |
|  | 9.38 | 48.6 | 0.05 | 40.8 |
| $DPA_{80}$-$MPC_{200}$-$DPA_{80}$ | 1.98 | 20.4 | 0.35 | 6.0 |
|  | 8.75 | 60.8 | 0.10 | 40.5 |

TABLE 4-continued

Summary of the DLS data for DPA-MPC-DPA triblock copolymers investigated in this study. The triblock copolymer concentration was 0.10 w/v % in all cases

| polymer | pH | D (nm) | Polydispersity | Intensity (kcps) |
|---|---|---|---|---|
| $DPA_{50}$-$MPC_{250}$-$DPA_{50}$ | 3.39 | 7.6 | 0.36 | 8.2 |
|  | 6.06 | 26.0 | 0.28 | 23.8 |
|  | 7.41 | 47.6 | 0.25 | 48.6 |
|  | 8.57 | 48.6 | 0.12 | 53.7 |
|  | 9.04 | 49.6 | 0.09 | 54.8 |
|  | 10.12 | 57.7 | 0.003 | 55.5 |
| $DPA_{30}$-$MPC_{300}$-$DPA_{30}$ | 1.88 | 14.6 | 0.35 | 7.4 |
|  | 9.62 | 43.4 | 0.11 | 42.5 |
| $DPA_{50}$-$MPC_{300}$-$DPA_{50}$ | 1.62 | 17.0 | 0.57 | 5.8 |
|  | 8.68 | 46.1 | 0.08 | 48.0 |
| $DPA_{100}$-$MPC_{300}$-$DPA_{100}$ | 2.88 | 26.2 | 0.43 | 9.8 |
|  | 8.96 | 60.1 | 0.12 | 47.1 |

EXAMPLE 2

HEMA-MPC-HEMA Triblock Copolymer Synthesis Via ATRP $HEMA_{50}$-$MPC_{200}$-$HEMA_{50}$ Triblock Copolymer.

MPC was polymerized first (8.02 g, 27.0 mmol) in 10 ml methanol, using [MPC]:[DEDBA]:[CuBr]:[bpy]=200:1:1:2. After 4 h, the monomer conversion was greater than 99%, and the MPC homopolymer obtained had a low polydispersity (Mw/Mn=1.16) with Mn=56,000 (vs. poly(ethylene oxide) standards). 2-Hydroxyethylmethacrylate (HEMA) monomer (1.76 g, 13.5 mmol, target Dp=50), was then added to this reaction solution. The reaction mixture was maintained under a dry nitrogen purge for the duration of the polymerization. On exposure to air after 24 h, the reaction solution turned blue, indicating aerial oxidation of the ATRP catalyst. $^1$H NMR studies indicated a HEMA monomer conversion of 96%. The reaction solution was passed through a silica gel column to remove the spent catalyst. After solvent evaporation, the copolymer was washed with excess THF to remove residual HEMA monomer and dried in a vacuum oven at room temperature to yield a colorless solid (8.86 grams). Table 5 summarises the polymerisation conditions.

These block copolymers were predicted to show temperature-responsive gelation characteristics, $HEMA_{50}$-$MPC_{200}$-$HEMA_{50}$ dissolves molecularly in water at room temperature as expected, and at higher temperatures especially at concentrations as high as 20% w/v, the viscosity increased.

TABLE 5

Summary of the conditions for the HEMA-MPC-HEMA triblock copolymer syntheses

| Triblock copolymer compotion | MPC g/mmol | DEDBA Initiator g/mmol | Cu(I)Br g/mmol | bpy g/mmol | DPA g/mmol |
|---|---|---|---|---|---|
| $HEMA_{50}$-$MPC_{100}$-$HEMA_{50}$ | 6.0/20.2 | 0.073/0.202 | 0.029/0.202 | 0.063/0.404 | 2.63/20.2 |
| $HEMA_{50}$-$MPC_{200}$-$HEMA_{50}$ | 8.02/27.0 | 0.049/0.135 | 0.019/0.135 | 0.042/0.270 | 1.76/13.5 |
| $HEMA_{100}$-$MPC_{200}$-$HEMA_{100}$ | 8.02/27.0 | 0.049/0.135 | 0.019/0.135 | 0.042/0.270 | 3.52/27.0 |
| $HEMA_{100}$-$MPC_{250}$-$HEMA_{100}$ | 10.02/33.7 | 0.049/0.135 | 0.019/0.135 | 0.042/0.270 | 3.52/27.0 |
| $HEMA_{100}$-$MPC_{300}$-$HEMA_{100}$ | 12.03/40.5 | 0.049/0.135 | 0.019/0.135 | 0.042/0.270 | 3.52/27.0 |

EXAMPLE 3

$DMA_{50}$-$MPC_{200}$-$DMA_{50}$ Triblock Copolymer

MPC was polymerized first (8.02 g, $2.7 \times 10^{-2}$ mol) in 10 ml methanol, using [MPC]:[DEDBA]:[CuBr]:[bpy]=200:1:1:2 under a nitrogen atmosphere at 20° C. After 4.0 h, the MPC conversion was greater than 98%, and the MPC homopolymer obtained had a low polydispersity (Mw/Mn=1.15 with Mn=56,000 vs. poly(ethylene oxide) standards. Then 2-dimethylaminoethyl methacrylate DMA monomer (2.12 g, $1.35 \times 10^{-2}$ mol, target Dp=50) was added to this reaction solution. After 24 h, $^1$H NMR studies indicated that both monomers had been consumed. The reaction solution was passed through a silica gel column to remove the spent ATRP catalyst, which resulted in the loss of around 10% copolymer due to adsorption onto the silica. After solvent evaporation, the solid copolymer was washed with excess n-hexane to remove any traces of residual DMA monomer, then freeze-dried overnight. The resulting colorless $DMA_{50}$-$MPC_{200}$-$DMA_{50}$ diblock copolymer (9.06 grams) had an Mn of 101,000 and an Mw/Mn of 1.53, as determined by aqueous GPC using poly (2-vinylpyridine) standards.

The block copolymer dissolves molecularly at room temperature, as expected, but the viscosity increased at higher temperatures even at concentrations as high as 20% w/v. The results are summarised in Table 6.

TABLE 6

Summary of the conditions for the DMA-MPC-DMA triblock copolymer syntheses.

| Triblock copolymer compotion | MPC g/mmol | DEDBA Initiator g/mmol | Cu(I)Br g/mmol | bpy g/mmol | DMA g/mmol |
|---|---|---|---|---|---|
| $DMA_{50}$-$MPC_{100}$-$DMA_{50}$ | 6.0/20.2 | 0.073/0.202 | 0.029/0.202 | 0.063/0.404 | 2/20.2 |
| $DMA_{100}$-$MPC_{200}$-$DMA_{100}$ | 8.02/27.0 | 0.049/0.135 | 0.019/0.135 | 0.042/0.270 | 4.24/27.0 |
| $DMA_{100}$-$MPC_{250}$-$DMA_{100}$ | 10.02/33.7 | 0.049/0.135 | 0.019/0.135 | 0.042/0.270 | 4.24/27.0 |
| $DMA_{150}$-$MPC_{250}$-$DMA_{150}$ | 10.02/33.7 | 0.049/0.135 | 0.019/0.135 | 0.042/0.270 | 5.30/40.5 |

* All synthesis were performed in 10 ml methanol.

EXAMPLE 4

DEA-MPC-DEA Triblock Copolymer

The MPC (10.02 grams; 33.7 mmol) was polymerized first in 10 ml methanol at 20° C. using standard schlenk techniques with a commercially available bifunctional ATRP initiator (diethyl meso-2,5-dibromoadipate, DEDBA, obtained from Aldrich; 0.049 grams; 0.135 mmol) and a Cu(I)Br/bpy catalyst (0.038 g, 0.270 mmol Cu(I)Br; 0.084 g, 0.540 mmol bpy). After 3 h, the MPC conversion was typically more than 99% as judged by $^1$H NMR. Then the DEA monomer (2.50 grams; 13.5 mmol) was added to this dark brown reaction solution. After 48 h, the reaction solution was passed through a silica gel column [silica gel 60 (0.063-0.200 mm) purchased from E. Merck (Darmstadt, Germany)] to remove the spent ATRP catalyst, which resulted in the loss of around 10% copolymer due to adsorption onto the silica. After solvent evaporation, the solid copolymer was washed with excess n-hexane to remove any traces of residual DEA monomer, then freeze-dried overnight to obtain a white solid.

The $^1$H NMR spectra of the $DEA_{50}$-$MPC_{250}$-$DEA_{50}$ triblock copolymer obtained under the above conditions showed a peak due to the DEA residues at δ 1.1 ppm (not present in the MPC homopolymer) and the relatively small peaks due to residual vinyl monomer signals at δ 5.5-6.5 ppm.

TABLE 7

Summary of the conditions for the DEA-MPC-DEA triblock copolymer syntheses

| Triblock copolymer compotion | MPC g/mmol | DEDBA Initiator g/mmol | Cu(I)Br g/mmol | bpy g/mmol | DEA g/mmol |
|---|---|---|---|---|---|
| $DEA_{50}$-$MPC_{250}$-$DEA_{50}$ | 10.02/33.7 | 0.049/0.135 | 0.038/0.270 | 0.084/0.540 | 2.5/13.5 |
| $DEA_{100}$-$MPC_{250}$-$DEA_{100}$ | 10.02/33.7 | 0.049/0.135 | 0.038/0.270 | 0.084/0.540 | 5.0/27.0 |

* All synthesis were performed in 10 ml methanol

TABLE 8

Summary of the triblock compositions, molecular weight data of the various DEA-MPC-DEA triblock copolymers

| target ABA triblock composition | Reaction time (h) | | Conversion, % | | Mn | | | Mw/Mn (GPC) | | Residual Cu by ICP-AES/ ppm |
|---|---|---|---|---|---|---|---|---|---|---|
| | homo | ABA triblock | homo | ABA triblock | Homo (GPC) | ABA Triblock(GPC) | ABA triblock (theory) | homo | ABA triblock | |
| $DEA_{50}$-$MPC_{250}$-$DEA_{50}$ | 4.5 | 30 | >98 | >98 | 68,000 | 103,000 | 93,000 | 1.17 | 1.62 | 0.6 |
| $DEA_{100}$-$MPC_{250}$-$DEA_{100}$ | 4.5 | 48 | >98 | >98 | 68,000 | 111,000 | 100,000 | 1.16 | 1.71 | 0.9 |

The triblock copolymers were molecularly dissolved in an acidic solution (pH<4) using HCl. On adjusting the stirred solution to pH 7-9 with NaOH, gelation was observed. The final gel pH was estimated using pH paper. The results are shown in Table 9.

TABLE 9

Summary of the chemical compositions and gelation behavior of the DEA-MPC-DEA triblock copolymers investigated in this study.

| Target ABA triblock copolymer composition | gelation behaviour at a given copolymer concentration | | | |
|---|---|---|---|---|
|  | 5% | 10% | 15% | 20% |
| $DEA_{50}$-$MPC_{250}$-$DEA_{50}$ | No gel | No free-standing gel | No free-standing gel | weak gel free-standing gel |
| $DEA_{100}$-$MPC_{250}$-$DEA_{100}$ |  |  |  |  |

The $^1H$ NMR spectra were obtained for the $DEA_{100}$-$MPC_{250}$-$DPA_{100}$ triblock copolymer: (a) as a free-flowing aqueous solution at pH 2 in $DCl/D_2O$ and (b) as a macroscopic physical gel at pH 9 after addition of NaOD. The signals assigned to the protonated DEA residues in spectrum (a) disappeared completely from spectrum (b) since the deprotonated DEA blocks become hydrophobic and hence much less solvated in the gel state.

EXAMPLE 5

MEMA-MPC-MEMA Triblock Copolymers

The MPC (10.02 grams; 33.7 mmol) was polymerized in 10 ml methanol at 20° C. using standard schlenk techniques with a commercially available bifunctional ATRP initiator (diethyl meso-2,5-dibromoadipate, DEDBA, obtained from Aldrich; 0.049 grams; 0.135 mmol) and a Cu(I)Br/bpy catalyst (0.038 g, 0.270 mmol Cu(I)Br; 0.084 g, 0.540 mmol bpy). After 3 h, the MPC conversion was typically more than 99% as judged by $^1H$ NMR. Then the 2-N-morpholino-ethyl methacrylate (MEMA) monomer (2.69 grams; 13.5 mmol) was added to this dark brown reaction solution. After 24 h, the reaction solution was passed through a silica gel column [silica gel 60 (0.063-0.200 mm) purchased from E. Merck (Darmstadt, Germany)] to remove the spent ATRP catalyst, which resulted in the loss of around 10% copolymer due to adsorption onto the silica. After solvent evaporation, the solid copolymer was freeze-dried overnight to obtain a white solid. The gelation behaviour upon addition of 1 M $NaSO_4$ at 20° C. to aqueous solutions was investigated. The results are shown in Table 12.

The $^1H$ NMR spectra of the $MEMA_{50}$-$MPC_{250}$-$MEMA_{50}$ triblock copolymer were obtained under the above conditions. A peak due to the MEMA residues was clear at δ 2.6-2.7 ppm and the relatively small peaks due to residual vinyl monomer signals were visible at δ 5.5-6.5 ppm.

TABLE 10

Summary of the conditions for the MEMA-MPC-MEMA triblock copolymer syntheses

| Triblock copolymer compotion | MPC g/mmol | DEDBA Initiator g/mmol | Cu(I)Br g/mmol | bpy g/mmol | MEMA g/mmol |
|---|---|---|---|---|---|
| $MEMA_{50}$-$MPC_{250}$-$MEMA_{50}$ | 10.02/33.7 | 0.049/0.135 | 0.038/0.270 | 0.084/0.540 | 2.69/13.5 |
| $MEMA_{100}$-$MPC_{250}$-$MEMA_{100}$ | 10.02/33.7 | 0.049/0.135 | 0.038/0.270 | 0.084/0.540 | 5.38/27.0 |

* All synthesis were performed in 10 ml methanol.

TABLE 11

Summary of the triblock compositions, molecular weight data of the various MEMA-MPC-MEMA triblock copolymers investigated in this study

| target ABA triblock composition | Reaction time (h) | | Conversion, % | | Mn | | | Mw/Mn (GPC) | | Residual Cu by ICP-AES/ ppm |
|---|---|---|---|---|---|---|---|---|---|---|
|  | homo | ABA triblock | homo | ABA triblock | Homo (GPC) | ABA Triblock (GPC) | ABA triblock (theory) | homo | ABA triblock |  |
| $MEMA_{50}$-$MPC_{250}$-$MEMA_{50}$ | 4.5 | 30 | >98 | >98 | 69,000 | 96,000 | 84,000 | 1.17 | 1.47 | 0.7 |
| $MEMA_{100}$-$MPC_{250}$-$MEMA_{100}$ | 4.5 | 48 | >98 | >98 | 68,000 | 121,000 | 114,000 | 1.16 | 1.52 | 0.6 |

TABLE 12

Summary of the chemical compositions and gelation behavior of the MEMA-MPC-MEMA triblock copolymers investigated in this study.

| Target ABA triblock copolymer composition | gelation behaviour at a given copolymer concentration in 1M NaSO$_4$ at 20° C. | | | |
|---|---|---|---|---|
| | 5% | 10% | 15% | 20% |
| MEMA$_{50}$-MPC$_{250}$-MEMA$_{50}$ | No | No | No | No |
| MEMA$_{100}$-MPC$_{250}$-MEMA$_{100}$ | No | weak gel | soft gel | free-standing gel |

Figure 10:
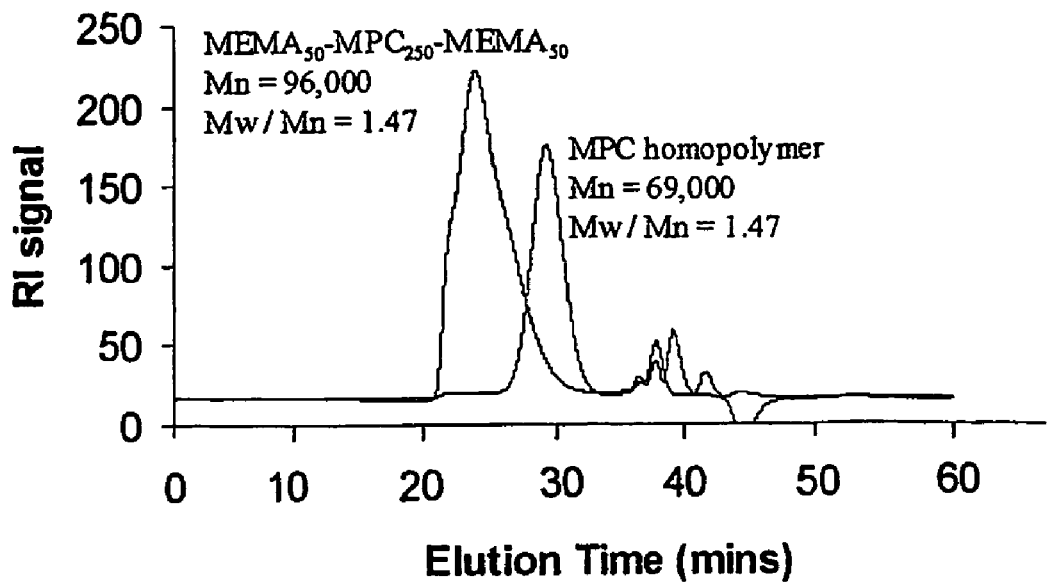

FIG. 10 shows GPC trace of the MEMA$_{50}$-MPC$_{250}$-MEMA$_{50}$ triblock copolymer and the corresponding MPC homopolymer precursor. This involved using two Aquagel columns (Aquagel 40 and Aquagel 30) connected to a Polymer Labs ERC-7517A refractive index detector. The solution comprising 0.5 M NaNO$_3$ and 0.05M TRIZMA Buffer at pH 7; PEO/PEG standards were used for calibration.

Figure 11:
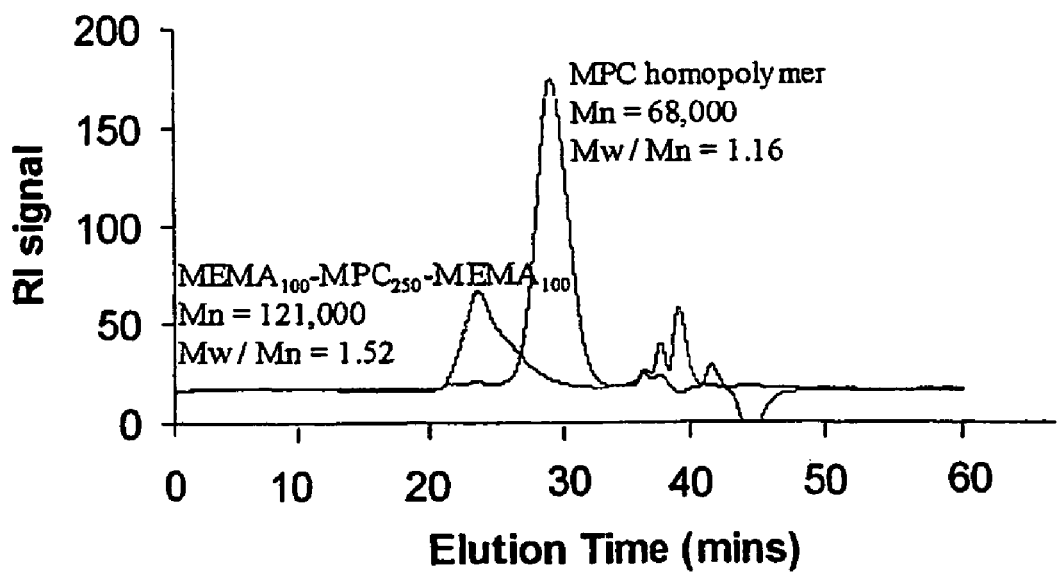

FIG. 11 shows GPC trace of the MEMA$_{100}$-MPC$_{250}$-MEMA$_{100}$ triblock copolymer and the corresponding MPC homopolymer precursor. This involved using two Aquagel columns (Aquagel 40 and Aquagel 30) connected to a Polymer Labs ERC-7517A refractive index detector. The solution comprising 0.2 M NaNO$_3$ and 0.05M TRIZMA Buffer at pH 7; PEO/PEG standards were used for calibration.

EXAMPLE 6

I-(MPC-DPA)$_3$ Diblock Copolymers 6.1

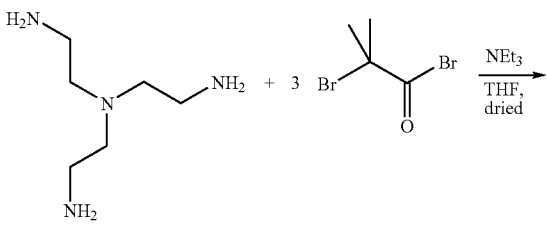

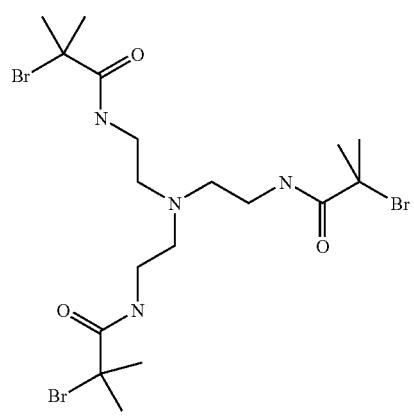

Tris-(2-aminoethyl)amine (10 ml, 9.77 g, 0.066 mol) was added to dry THF (200 ml). Excess triethylamine (60 ml) was then added and the mixture was stirred under nitrogen atmosphere. The solution was cooled in an ice bath and 2-bromoisobutyryl bromide (26 ml, 46 g, 0.2 mol) was added dropwise from a dropping funnel. This addition was carried out over a period of approximately 1 h. The mixture was then stirred for another 2 h. The white precipitate formed was then removed by filtration and the pale yellow solution was concentrated under vacuum at 30° C. The viscous yellowish liquid was cooled in an ice bath. The solid that formed was stirred in distilled water, filtered and washed with distilled water. The pale yellow powder obtained was then dried under vacuum. (Yield: 78%)

6.2 A typical synthesis for the three-arm I-(MPC-DPA)$_3$ star diblock copolymer was carried out as follows. The MPC (9.01 grams; 30.4 mmol) was polymerized in 10 ml methanol at 20° C. using standard schlenk techniques with a trifunctional amide-based ATRP initiator (0.040 grams; 0.068 mmol; synthesised by Dr. R. Narain) and a Cu(I)Br/bpy catalyst (0.029 g, 0.202 mmol Cu(I)Br; 0.063 g, 0.405 mmol bpy). After 5 h, the MPC conversion was typically more than 98% as judged by $^1$H NMR, and the MPC homopolymer obtained had a relatively high polydispersity (Mw/Mn=2.07 vs. poly (2-vinylpyridine) standards, see Table 14). Then the DPA monomer (2.17 grams; 10.1 mmol) was added to this dark brown reaction solution. After 3 days further polymerisation, the reaction solution was passed through a silica gel column [silica gel 60 (0.063-0.200 mm) purchased from E. Merck (Darmstadt, Germany)] to remove the spent ATRP catalyst, which resulted in the loss of around 15% copolymer due to adsorption onto the silica. After solvent evaporation, the solid copolymer was washed with excess n-hexane to remove any traces of residual DPA monomer, then freeze-dried overnight to obtain a white solid (10.6 grams).

Figure 12:
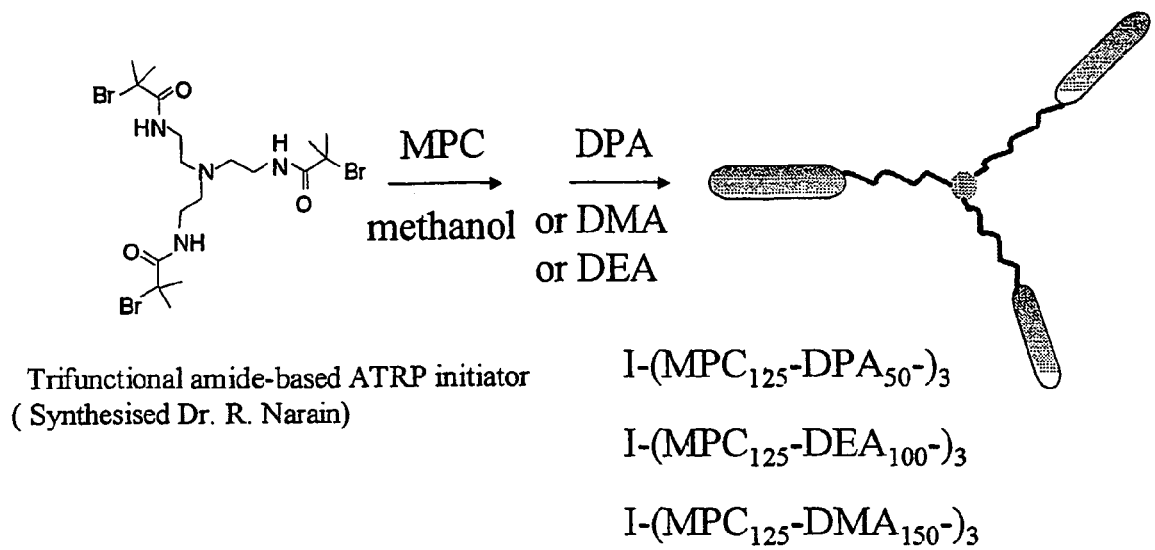

FIG. 12 shows the reaction scheme for the synthesis of the I-(MPC-DPA)$_3$ star diblock copolymers via Atom Transfer Radical Polymerization (ATRP) using a trifunctional amide-based ATRP initiator (I).

The $^1$H NMR spectra of the I-(MPC$_{150}$-DPA$_{50}$)$_3$ star diblock copolymers obtained under the above conditions were determined. The peak due to the DPA residues at δ 1.1 ppm was visible and the relatively small peaks due to residual vinyl monomer signals at δ 5.5-6.5 ppm.

TABLE 13

Summary of the conditions for the I-(MPC-DPA)$_3$ star diblock copolymer syntheses.

| Star diblock copolymer composition | MPC g/mmol | Initiator g/mmol | Cu(I)Br g/mmol | bpy g/mmol | DPA g/mmol |
|---|---|---|---|---|---|
| I-(MPC$_{125}$-DPA$_{50}$)$_3$ | 15.03/50.6 | 0.08/0.135 | 0.019/0.135 | 0.042/0.270 | 4.33/20.3 |
| I-(MPC$_{125}$-DPA$_{100}$)$_3$ | 15.03/50.6 | 0.08/0.135 | 0.057/0.405 | 0.126/0.810 | 8.67/40.5 |
| I-(MPC$_{100}$-DPA$_{50}$)$_3$ | 12.03/40.5 | 0.08/0.135 | 0.057/0.405 | 0.126/0.810 | 4.33/20.2 |
| I-(MPC$_{150}$-DPA$_{50}$)$_3$ | 9.01/30.4 | 0.04/0.068 | 0.029/0.202 | 0.063/0.405 | 2.17/10.1 |
| I-(MPC$_{150}$-DPA$_{80}$)$_3$ | 9.01/30.4 | 0.04/0.068 | 0.029/0.202 | 0.063/0.405 | 3.48/16.3 |
| I-(MPC$_{150}$-DPA$_{100}$)$_3$ | 9.01/30.4 | 0.04/0.068 | 0.029/0.202 | 0.063/0.405 | 4.33/20.2 |

\* All synthesis were performed in 10 ml methanol.

TABLE 14

Summary of the star diblock compositions and molecular weight data of I-(MPC-DPA)$_3$ star diblock copolymers

| Star diblock copolymer composition | Reaction time | | Conversion, % | | Mn | | | Mw/Mn (GPC) | | Residual Cu by ICP-AES/ppm |
|---|---|---|---|---|---|---|---|---|---|---|
| | star homo (h) | star diblock (days) | homo | star diblock | homo (GPC) | star diblock (GPC) | star diblock (theory) | homo | star diblock | |
| I-(MPC$_{125}$-DPA$_{50}$)$_3$ | 4.5 | 2 | >98 | >98 | 103,000 | 198,000 | 145,000 | 2.07 | 2.36 | 0.3 |
| I-(MPC$_{125}$-DPA$_{100}$)$_3$ | 4.5 | 3 | >98 | >95 | 101,000 | 133,000 | 178,000 | 2.11 | 2.53 | 6.5 |
| I-(MPC$_{100}$-DPA$_{50}$)$_3$ | 4 | 2 | >98 | >98 | 82,000 | 123,000 | 123,000 | 2.01 | 2.45 | 5.0 |
| I-(MPC$_{150}$-DPA$_{50}$)$_3$ | 5 | 3 | >98 | >98 | 115,000 | 168,000 | 168,000 | 2.09 | 2.20 | 3.4 |
| I-(MPC$_{150}$-DPA$_{80}$)$_3$ | 5 | 3 | >98 | >95 | 113,000 | 155,000 | 188,000 | 2.10 | 2.43 | 2.4 |
| I-(MPC$_{150}$-DPA$_{100}$)$_3$ | 5 | 3 | >98 | >95 | 113,000 | 185,000 | 201,000 | 2.06 | 2.48 | 6.9 |

Figure 13:
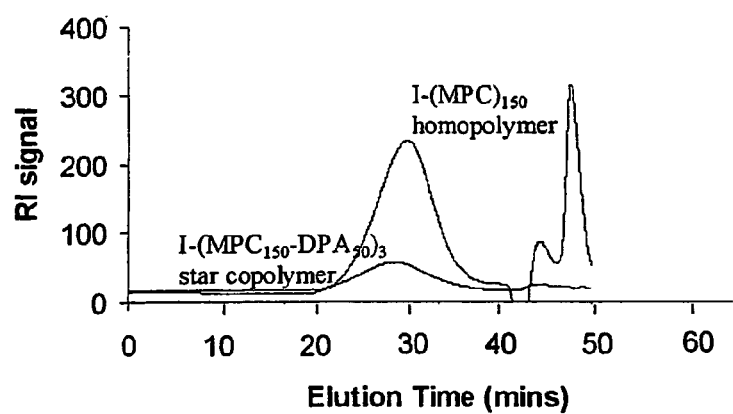

FIG. 13 shows the GPC trace of the I-(MPC$_{150}$-DPA$_{50}$)$_3$ star diblock copolymer and its MPC star homopolymer precursor. This involved using two ViscoGEL columns (G5000 PWXL and G2500 PWXL) connected in series to a Polymer Labs ERC-7517A refractive index detector. The eluent comprised 0.5 M acetic acid and 0.3M NaSO$_4$ at pH 2; poly(2-vinylpyridine) standards (PSS, Germany) were used for calibration.

Gelation properties were determined in a similar fashion to example 4, by changing the pH from 2 to 9. The results are shown in Table 15.

TABLE 15

Summary of the chemical compositions and gelation behavior of the I-(MPC-DPA)$_3$ star diblock copolymers.

| Target ABA triblock copolymer composition | gelation behaviour at a given copolymer concentration | | | |
|---|---|---|---|---|
| | 1% | 3% | 5% | 10% |
| I-(MPC$_{125}$-DPA$_{50}$)$_3$ | weak gel | gel | free-standing gel | free-standing gel |
| I-(MPC$_{125}$-DPA$_{100}$)$_3$ | gel | free-standing gel | free-standing gel | free-standing gel |
| I-(MPC$_{100}$-DPA$_{50}$)$_3$ | No | weak gel | gel | free-standing gel |
| I-(MPC$_{150}$-DPA$_{50}$)$_3$ | No | gel | free-standing gel | free-standing gel |
| I-(MPC$_{150}$-DPA$_{80}$)$_3$ | No | gel | free-standing gel | free-standing gel |
| I-(MPC$_{150}$-DPA$_{100}$)$_3$ | gel | free-standing gel | free-standing gel | free-standing gel |

The $^1$H NMR spectra were obtained for the I-(MPC$_{125}$-DPA$_{50}$)$_3$ star diblock copolymer: (a) as a free-flowing aqueous solution at pH 2 in DCl/D$_2$O and (b) as a macroscopic physical gel at pH 9 after addition of NaOD. The signals assigned to the protonated DPA residues in spectrum at 1.3 ppm (a) disappear completely from spectrum (b) since the deprotonated DPA blocks become hydrophobic and hence much less solvated in the gel state.

EXAMPLE 7

I-(MPC$_{125}$-DEA$_{100}$)$_3$ Star Diblock Copolymer

The MPC (15.03 grams; 50.6 mmol) was polymerized first in 10 ml methanol at 20° C. using standard schlenk techniques with the trifunctional amide-based ATRP initiator synthesised in Example 6.1 (0.08 grams; 0.135 mmol) and a Cu(I)Br/bpy catalyst (0.057 g, 0.405 mmol Cu(I)Br; 0.126 g, 0.810 mmol bpy). After 4.5 h, the MPC conversion was typically more than 98% as judged by $^1$H NMR. Then the DEA monomer (7.50 grams; 40.5 mmol) was added to this dark brown reaction solution. After 3 days further polymerisation, the reaction solution was passed through a silica gel column [silica gel 60 (0.063-0.200 mm) purchased from E. Merck (Darmstadt, Germany)] to remove the spent ATRP catalyst, which resulted in the loss of around 15% copolymer due to adsorption onto the silica. After solvent evaporation, the solid copolymer was washed with excess n-hexane to remove any traces of residual DEA monomer, then freeze-dried overnight to obtain a white solid.

The $^1$H NMR spectra of the I-(MPC$_{125}$-DEA$_{100}$)$_3$ star diblock copolymer and its corresponding star homopolymer precursor obtained under the above conditions were observed. The peak due to the DEA residues at d 1.1 ppm was visible and the relatively small peaks due to residual vinyl monomer is signals at d 5.5-6.5 ppm.

FIG. 14 shows the GPC trace of the I-(MPC$_{125}$-DEA$_{100}$)$_3$ star diblock copolymers. This involved using two ViscoGEL columns (G5000 PWXL and G2500 PWXL) connected to a Polymer Labs ERC-7517A refractive index detector. The eluent comprised 0.5 M acetic acid and 0.3M NaSO$_4$ at pH 2; poly(2-vinylpyridine) standards (PSS, Germany) were used for calibration.

The $^1$H NMR spectra were obtained for the I-(MPC$_{125}$-DEA$_{100}$)$_3$ star diblock copolymer: (a) as a free-flowing aqueous solution at pH 2 in DCl/D$_2$O and (b) as a macroscopic physical gel at pH 9 after addition of NaOD. The signals assigned to the protonated DEA residues in spectrum (a) disappear completely from spectrum (b) since the deprotonated DEA blocks become hydrophobic and hence much less solvated in the gel state.

A free-flowing aqueous solution was formed at pH 2 and a physical gel formed at pH 9 by the I-(MPC$_{125}$-DEA$_{100}$)$_3$ star diblock copolymer at 5% w/v.

EXAMPLE 8

I-(MPC-DMA)$_3$ Star Diblock Copolymers

The MPC (15.03 grams; 50.6 mmol) was polymerized first in 10 ml methanol at 20° C. using standard schlenk techniques with the trifunctional amide-based ATRP initiator synthesised in Example 6.1 (0.08 grams; 0.135 mmol) and a Cu(I)Br/bpy catalyst (0.057 g, 0.405 mmol Cu(I)Br; 0.126 g, 0.810 mmol bpy). After 4 h, the MPC conversion was typically more than 98% as judged by $^1$H NMR. Then the DMA monomer (3.19 grams; 20.3 mmol) was added to this dark brown reaction solution. After 3 days further polymerisation, the reaction solution was passed through a silica gel column [silica gel 60 (0.063-0.200 mm) purchased from E. Merck (Darmstadt, Germany)] to remove the spent ATRP catalyst, which resulted in the loss of around 15% copolymer due to adsorption onto the silica. After solvent evaporation, the solid copolymer was washed with excess n-hexane to remove any traces of residual DMA monomer, then freeze-dried overnight to obtain a white solid.

An aqueous solution of the desired concentration was prepared was prepared in either doubly-distilled, de-ionised water or PBS buffer at 10° C. to ensure molecular dissolution. Then this aqueous copolymer solution was placed in an oil bath and heated up to the desired temperature (typically 37° C.) to induce gelation. At both temperatures gelation was confirmed by tube inversion experiments.

TABLE 16

Summary of the conditions for the I-(MPC-DMA)$_3$ star diblock copolymer syntheses.

| Star diblock copolymer composition | MPC g/mmol | Initiator g/mmol | Cu(I)Br g/mmol | bpy g/mmol | DMA g/mmol |
|---|---|---|---|---|---|
| I-(MPC$_{125}$-DMA$_{50}$)$_3$ | 15.03/50.6 | 0.08/0.135 | 0.057/0.405 | 0.126/0.810 | 3.19/20.3 |
| I-(MPC$_{125}$-DMA$_{100}$)$_3$ | 15.03/50.6 | 0.08/0.135 | 0.057/0.405 | 0.126/0.810 | 6.37/40.5 |
| I-(MPC$_{125}$-DMA$_{150}$)$_3$ | 15.03/50.6 | 0.08/0.135 | 0.057/0.405 | 0.126/0.810 | 9.55/60.7 |
| I-(MPC$_{150}$-DMA$_{150}$)$_3$ | 9.01/30.4 | 0.04/0.068 | 0.029/0.202 | 0.063/0.405 | 4.77/30.4 |
| I-(MPC$_{100}$-DMA$_{150}$)$_3$ | 12.03/40.5 | 0.08/0.135 | 0.057/0.405 | 0.126/0.810 | 9.55/60.7 |

*All synthesis were performed in 10 ml methanol.

TABLE 17

Summary of the star diblock compositions, molecular weight data of the I-(MPC-DMA)$_3$ star diblock copolymers

| Star diblock copolymer composition | Reaction time homo (h) | Reaction time diblock (days) | Conversion, % homo | Conversion, % star diblock | Mn homo (Viscotick GPC) | Mn star (Aquage IGPC) | Mn diblock (theory) | Mw/Mn (GPC) homo | Mw/Mn (GPC) star diblock | Residual Cu by ICP-AES/ppm |
|---|---|---|---|---|---|---|---|---|---|---|
| I-(MPC$_{125}$-DMA$_{50}$)$_3$ | 4.5 | 2 | >98 | >98 | 148,000 | 130,000 | 136,000 | 2.06 | 1.51 | 2.6 |
| I-(MPC$_{125}$-DMA$_{100}$)$_3$ | 4.5 | 3 | >98 | >96 | 103,000 | 146,000 | 160,000 | 2.07 | 1.72 | 1.9 |
| I-(MPC$_{125}$-DMA$_{150}$)$_3$ | 4.5 | 3 | >98 | >98 | 113,000 | 151,000 | 183,000 | 2.11 | 1.75 | 1.9 |
| I-(MPC$_{150}$-DMA$_{150}$)$_3$ | 5.0 | 3 | >96 | >98 | 114,000 | 155,000 | 206,000 | 1.98 | 1.86 | 1.5 |
| I-(MPC$_{100}$-DMA$_{150}$)$_3$ | 4.0 | 3 | >99 | >99 | 100,000 | 126,000 | 161,000 | 1.86 | 1.82 | 2.8 |

TABLE 18

Summary of the chemical compositions and gelation behavior of the I-(MPC-DMA)₃ star diblock copolymers upon temperature change

| Target ABA triblock copolymer composition | gelation behaviour at a given copolymer concentration | | | |
|---|---|---|---|---|
| | 1% | 3% | 5% | 10% |
| I-(MPC$_{125}$-DMA$_{50}$)$_3$ | No | No | gel | free-standing gel |
| I-(MPC$_{125}$-DMA$_{100}$)$_3$ | No | No | weak gel | gel |
| I-(MPC$_{125}$-DMA$_{150}$)$_3$ | gel | free-standing gel | free-standing gel | free-standing gel |
| I-(MPC$_{150}$-DMA$_{150}$)$_3$ | No | weak gel | gel | free-standing gel |
| I-(MPC$_{100}$-DMA$_{150}$)$_3$ | weak gel | gel | free-standing gel | free-standing gel |

Variable temperature $^1$H NMR studies of the thermo-responsive I-(MPC$_{125}$-DMA$_{150}$)$_3$ star diblock copolymer were conducted. The attenuation of the NMR signals assigned to the DMA residues at 2.5 ppm as these blocks become less solvated and more immobile in the gel state was apparent.

EXAMPLE 9

I-(MPC$_{125}$-MEMA$_{100}$)$_3$ Star Diblock Copolymer

The MPC (15.03 grams; 50.6 mmol) was polymerized first in 10 ml methanol at 20° C. using standard schlenk techniques with the trifunctional amide-based ATRP initiator (0.08 grams; 0.135 mmol) and a Cu(I)Br/bpy catalyst (0.057 g, 0.405 mmol Cu(I)Br; 0.126 g, 0.810 mmol bpy). After 4.5 h, the MPC conversion was typically more than 98% as judged by $^1$H NMR. Then the MEMA monomer (8.07 grams; 40.5 mmol) was added to this dark brown reaction solution. After 3 days further polymerisation, the reaction solution was passed through a silica gel column [silica gel 60 (0.063-0.200 mm) purchased from E. Merck (Darmstadt, Germany)] to remove the spent ATRP catalyst, which resulted in the loss of around 15% copolymer due to adsorption onto the silica. After solvent evaporation, the solid copolymer was freeze-dried overnight to obtain a white solid.

The $^1$H NMR spectra were determined of the I-(MPC$_{125}$-MEMA$_{100}$)$_3$ star diblock copolymer and its corresponding I-(MPC)$_{125}$ star homopolymer precursor obtained under the above conditions. The appearance of a new peak compared to the star polymers to example 6 due to the MEMA residues at δ 2.6-2.7 ppm was noted.

EXAMPLE 10

Thermoreversible Three-arm Star Gelators (1) Synthesis of PPOMA Macromonomer.

Methacryloyl chloride (6.27 g, 60 mmol, 6.0 eq.) was added dropwise to a toluene solution (100 mL) of monohydroxy-capped poly(propylene oxide) [PPO—OH] (20.00 g, 10 mmol) and triethylamine (6.06 g, 60 mmol, 6.0 eq.) under nitrogen. This mixture was stirred for seven days and then filtered to remove the insoluble inorganic salt. The solution was then washed three times with an aqueous solution of 0.1 M Na$_2$CO3, then three times with doubly-distilled water. The solution was dried over MgSO$_4$ and the solvent is was removed under reduced pressure. The final PPOMA product was obtained as a slightly yellow liquid (17.8 g, yield 85%) and was stored in a freezer in the absence of light prior to use.

10.2 Synthesis of TrisE Initiator

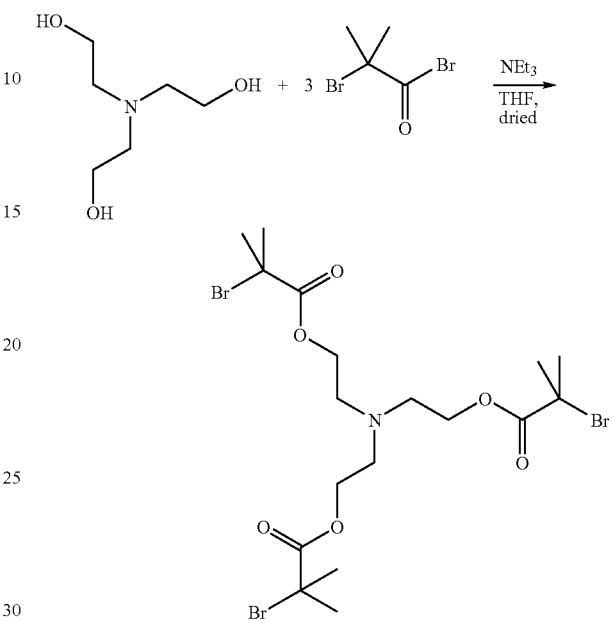

Triethanolamine (5.0 g, 33.5 mmol) was added to dry THF (200 ml). Excess triethylamine (60 ml) was then added and the mixture was stirred under nitrogen atmosphere. After cooling the solution in an ice bath, 2-bromoisobutyryl bromide (24.7 ml, 45.98 g, 0.20 mol) was added dropwise to the mixture from a dropping funnel. The addition was carried out for 1 h and the solution slowly became reddish brown in colour. After stirring the reaction mixture for another 2 h, the triethylammonium chloride salt was removed by filtration and the resulting clear solution was concentrated under vacuum at 30° C. The concentrated solution was stirred with 0.1 M Na$_2$CO$_3$ to hydrolyse the residual unreacted 2-bromoisobutyryl bromide. The product was then extracted three times with dichloromethane in a separating funnel. The combined dichloromethane extract was first dried with magnesium sulfate and then concentrated to give a dark reddish brown oil, which was stored at 4° C. (Yield: 72%).

10.3 I-[MPC$_{125}$-(DMA$_{50}$/DEA$_{50}$/PPOMA$_3$)]$_3$ Star Diblock Copolymer.

A typical synthesis for the I-[MPC$_{125}$-(DMA$_{50}$/DEA$_{50}$/PPOMA$_3$)]$_3$ three-arm star diblock copolymer was carried out as follows. The MPC (3.70 grams; 12.5 mmol) was polymerised in methanol at 20° C. using standard Schlenk techniques using the trifunctional TrisE initiator (0.0198 grams; 0.033 mmol, Target Dp for each MPC arm is 125) and a Cu(I)Br/2 bpy catalyst (0.0143 g, 0.10 mmol Cu(I)Br; 0.0312 g, 0.20 mmol bpy). After 70 min, the MPC conversion was typically more than 92% as judged by $^1$H NMR and typical aqueous GPC data indicated an M$_n$ of around 42,500 and an M$_w$/M$_n$ of 1.47. Then the DMA (0.786 g; 5.0 mmol), DEA (0.926 g, 5.0 mmol) and PPOMA (0.621 g, 0.30 mmol) [overall target Dp=50+50+3=103] comonomer mixture dissolved in 4.0 ml methanol was added to the dark brown reaction solution. After 48 h (total comonomer conversion was around 90%), the final reaction solution was passed through a silica gel column [silica gel 60 (0.063-0.200 mm) purchased from E. Merck (Darmstadt, Germany)] to remove the spent ATRP catalyst, which resulted in the loss of around 10% copolymer due to adsorption onto the silica. After solvent evaporation, the solid copolymer was freeze-dried overnight to obtain a yellowish-white solid. (Yield: 5.5 grams).

Other copolymers were formed using the components and conditions in Table 19 below. Tris A was synthesised and in Example 6.1 above. The yields are also shown in Table 19 (ND means not determined). The gelation properties of a number of solutions is shown in Table 20.

TABLE 19

Formulation details for the ATRP synthesis of MPC-based star diblock copolymers

| Example # | Initiator Type | Target Copolymer Structure | Solvent | MPC (mmol) | DMA (mmol) | DEA (mmol) | PPOMA (mmol) | HEMA (mmol) | Cu content (ppm) | Total conv. |
|---|---|---|---|---|---|---|---|---|---|---|
| Ex10/1 | TrisA | I-[MPC$_{125}$-(DMA$_{93}$/PPOMA$_7$)]$_3$ | methanol/water | 12.5 | 9.3 | — | 0.7 | — | ND | 80% |
| Ex10/2 | TrisA | I-[MPC$_{125}$-(DMA$_{90}$/PPOMA$_{10}$)]$_3$ | methanol/water | 12.5 | 9.0 | — | 1.0 | — | ND | 92% |
| Ex10/3 | TrisA | I-[MPC$_{125}$-(DMA$_{93}$/PPOMA$_7$)]$_3$ | methanol | 12.5 | 9.3 | — | 0.7 | — | ND | 98% |
| Ex10/4 | TrisA | I-[MPC$_{125}$-(DMA$_{93}$/PPOMA$_7$)]$_3$ | methanol | 12.5 | 9.3 | — | 0.7 | — | ND | 90% |
| Ex10/5 | TrisE | I-[MPC$_{125}$-(DMA$_{93}$/PPOMA$_7$)]$_3$ | methanol | 12.5 | 9.3 | — | 0.7 | — | ND | 99% |
| Ex10/6 | TrisE | I-[MPC$_{125}$-(DMA$_{95}$/PPOMA$_5$)]$_3$ | methanol | 12.5 | 9.5 | — | 0.5 | — | ND | ND |
| Ex10/7 | TrisE | I-[MPC$_{125}$-(DMA$_{97}$/PPOMA$_3$)]$_3$ | methanol | 12.5 | 9.7 | — | 0.3 | — | <1.0 | 90% |
| Ex10/8 | TrisE | I-[MPC$_{125}$(DMA$_{50}$/DEA$_{50}$)]$_3$ | methanol/water | 12.5 | 5.0 | 5.0 | — | — | <1.0 | 92% |
| Ex10/9 | TrisA | I-[MPC$_{125}$(DMA$_{50}$/DEA$_{50}$)]$_3$ | methanol | 12.5 | 5.0 | 5.0 | — | — | <1.0 | 90% |
| Ex10/10 | TrisE | I-[MPC$_{125}$-(DMA$_{50}$/DEA$_{50}$/PPOMA$_3$)]$_3$ | methanol | 12.5 | 5.0 | 5.0 | 0.3 | — | 1.5 | ND |
| Ex10/11 | TrisE | I-[MPC$_{125}$-(DMA$_{70}$/DEA$_{30}$/PPOMA$_5$)]$_3$ | methanol | 12.5 | 7.0 | 3.0 | 0.5 | — | ND | ND |
| Ex10/12 | TrisA | I-[MPC$_{125}$-(HEMA$_{93}$/PPOMA$_7$)]$_3$ | methanol | 12.5 | — | — | 0.7 | 9.3 | ND | 90% |
| Ex10/13 | TrisE | I-[MPC$_{125}$-(HEMA$_{97}$/PPOMA$_3$)]$_3$ | methanol | 12.5 | — | — | 0.3 | 9.7 | ND | 91% |
| Ex10/14 | TrisE | I-[MPC$_{125}$/PPOMA$_{10}$]$_3$ | methanol | 12.5 | — | — | 1.0 | — | ND | 85% |
| Ex10/15 | TrisE | I-(MPC$_{125}$-DMA$_{100}$)$_3$ | methanol | 12.5 | 10.0 | — | — | — | ND | 90% |

TABLE 20

Summary of the chemical compositions and gelation behavior of the various star diblock copolymers study

| | Target star | gelation behaviour | |
|---|---|---|---|
| Ex | copolymer composition | Aqueous solution | PBS buffer |
| 10/15 | I-[MPC125-DMA100]3 | Weak gel at 20% & 80° C. | |
| 10/2 | I-[MPC125-(DMA90/PPOMA10)]3 | 20% at 37° C. | 20% at 37° C. |
| 10/3 | I-[MPC125-(DMA93/PPOMA7)]3 | 20% at 37° C. | 20% at 37° C. |
| 10/4 | I-[MPC125-(DMA93/PPOMA7)]3 | 20% at 37° C. | 20% at 37° C. |
| 10/5 | I-[MPC125-(DMA93/PPOMA7)]3 | 20% at 37° C. | 15% at 37° C. |
| 10/6 | I-[MPC125-(DMA95/PPOMA5)]3 | 8% at 20° C. | 7% at 37° C. |
| 10/7 | I-[MPC125-(DMA97/PPOMA3)]3 | 6%, free standing gel at 37° C. | 5%, weak free standing gel at 37° C. |
| 10/8 | I-[MPC125(DMA50/DEA50)]3 | 7%, free standing gel at 37° C. | 6%, weak gel at 37° C. |
| 10/9 | I-[MPC125(DMA50/DEA50)]3 | 8%, free standing gel at 37° C. | 7%, weak free standing gel at 37° C. |
| 10/10 | I-[MPC125-(DMA50/DEA50/PPOMA3)]3 | 6%, free standing gel at 37° C. | 5%, free standing gel at 37° C. |
| 10/11 | I-[MPC125-(DMA70/DEA30/PPOMA5)]3 | 7%, free standing gel at 37° C. | 7%, free standing gel at 37° C. |
| 10/12 | I-[MPC125-(HEMA93/PPOMA7)]3 | No gel at 20% | No gel at 20% |
| 10/13 | I-[MPC125-(HEMA97/PPOMA3)]3 | No gel at 20% | No gel at 20% |

EXAMPLE 11

Thermo-Responsive N-Isopropylacrylamide Based Copolymer Gelators 11.1 NIPAM$_n$-MPC$_{250}$-NIPAM$_n$ Triblock Copolymer Examples A typical synthesis of a NIPAM$_n$-MPC$_{250}$-NIPAM$_n$ triblock copolymer was carried out in two steps, as described in the reaction scheme below. In the first step the Br-MPC$_{250}$-Br macro-initiator was prepared as follows. MPC (3.72 g, 12.5 mmol) was polymerized in 5 ml methanol at 20° C. using standard Schlenk techniques with a commercially available bifunctional ATRP initiator (diethyl meso-2,5-dibromoadipate, DEDBA, obtained from Aldrich; 18 mg, 0.05 mmol) and a Cu(I Br/2 bpy catalyst (14.4 mg, 0.10 mmol Cu(I)Br; 31.2 mg, 0.20 mmol bpy). After 4.5 h the MPC conversion was typically more than 98% as judged by $^1$H NMR. Aqueous GPC analysis (vs. poly(ethylene oxide) calibration standards) indicated that the MPC homopolymer $M_n$ was 44,800 and the $M_w/M_n$ was 1.45. The reaction flask was immersed in liquid nitrogen to terminate this first-stage polymerization, excess methanol was added and the resulting solution was then passed through a silica gel column [silica gel 60 (0.063-0.200 mm) purchased from E. Merck (Darmstadt, Germany)] to remove the spent ATRP catalyst. After solvent evaporation, the solid polymer was dissolved in distilled water and freeze-dried overnight. The bifunctional MPC macro-initiator was obtained as a white powder, 3.3 g. The second-stage polymerization to obtain the NIPAM$_n$-MPC$_{250}$-NIPAM$_n$ ABA-type triblock copolymer was carried out as follows. In a Schlenk flask N-isopropylacrylamide (NIPAM; 1.13 g; 10 mmol) and Cu(I)Br/Me$_4$Cyclam (1,4,8,11-tetramethyl-1,4,8,11-tetraazacyclotetradecane) catalyst (7.2 mg, 0.05 mmol Cu(I)Br; 12.8 mg, 0.05 mmol Me$_4$Cyclam) were added to 10 ml degassed methanol and stirred in an ice bath to form an homogeneous solution under a nitrogen atmosphere. The MPC bifunctional initiator (1.84 g; 0.05 mmol bromine) was degassed and added under nitrogen atmosphere and the NIPAM polymerization was allowed to continue until $^1$H NMR analysis indicated no further change in the conversion after 2 hours. Excess methanol was then added to dilute the reaction solution, which was passed though a silica gel column to remove the spent catalyst. After solvent evaporation, the isolated solid was dissolved in distilled water and freeze-dried overnight to obtain a white powder (2.1 g). The copper content measured by ICP-AES was 1.5 ppm. Aqueous GPC analyses of these NIPAM-MPC-NIPAM triblock copolymers has not yet proved successful.

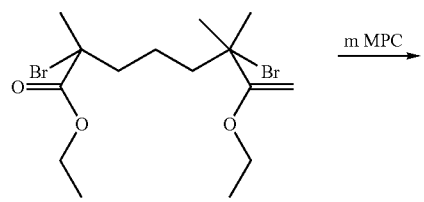

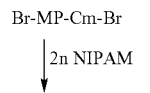

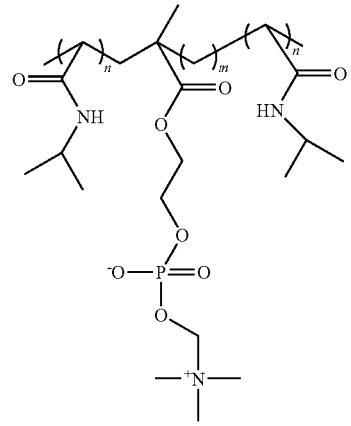

This shows the reaction scheme for the synthesis of MPC bifunctional macro-initiator and NIPAM$_n$-MPC$_m$-NIPAM$_n$ triblock copolymers.

11.2 Thermo-Responsive Gelation Behavior of ABA Triblock Copolymers 9.0 w/w % purely aqueous and phosphate buffer (pH 7.1) solutions of the NIPAM$_n$-MPC$_m$-NIPAM$_n$ triblock copolymers form physical gels at or above 39° C. Gelation is readily confirmed by tube inversion experiments. The temperature range over which gelation occurs is very narrow (<1° C.) gelation was fully reversible: each gel redissolved to form the original free-flowing due to the relatively sharp thermo-responsiveness of polyNIPAM. Moreover, solution on cooling.

11.3 I-[MPC$_{125}$-NIPAM$_n$]$_3$ Three-Arm Star Diblock Copolymer Examples

The trifunctional TrisA initiator derived from tris-(2-aminoethyl)amine was synthesized as described previously. A typical synthesis of a I-(MPC$_{125}$-NIPAM$_n$)$_3$ of a three-arm star diblock copolymer was carried out in two steps as outlined in the reaction scheme below, similar to the protocol used for preparing the ABA triblock copolymers. First a three-arm star I-(MPC$_{125}$-Br)$_3$ macro-initiator was carried out as follows. MPC (3.72 g, 12.5 mmol) was polymerized in 5 ml methanol at 20° C. using standard Schlenk techniques with the TrisA initiator (19.9 mg, 0.033 mmol) and a Cu(I) Br/2 bpy catalyst (14.4 mg, 0.1 mmol Cu(I)Br; 31.2 mg, 0.2 mmol bpy). After 3.5 h the MPC conversion was typically more than 98% as judged by $^1$H NMR. Aqueous GPC analysis (vs. poly(ethylene oxide) standards) indicated that the MPC homopolymer $M_n$ was 58,000 and the $M_w/M_n$ was 1.49. The reaction flask was immersed in liquid nitrogen to terminate the polymerization, excess methanol was added and the resulting diluted solution was passed though a silica gel column [silica gel 60 (0.063-0.200 mm) purchased from E. Merck (Darmstadt, Germany)] to remove the spent ATRP catalyst. After solvent evaporation the solid was dissolved in distilled water and freeze-dried overnight. The trifunctional MPC macro-initiator was obtained as a white powder (3.2 g). The second step to prepare the three arm I-(MPC$_{125}$-NIPAM$_n$)$_3$ star diblock copolymer was carried out as follows. To a Schlenk flask was added N-isopropylacrylamide (NIPAM; 0.61 g; 54 mmol), Cu(I)Br/Me$_4$Cyclam catalyst (3.9 mg, 0.027 mmol Cu(I)Br; 6.9 mg, 0.054 mmol Me₄Cyclam) and 1.0 g trifunctional macro-initiator (corresponding to 0.09 mmol macro-initiator) in 5, 10 and 20 ml methanol in an ice bath until no further change in the NIPAM conversion was observed by ¹H NMR. Excess methanol was added to dilute the reaction solution, which was passed through a silica gel column to remove the spent catalyst. After solvent evaporation, the resulting solid was dissolved in distilled water and freeze-dried overnight. A white powder was obtained (1.8 g). Three star diblock copolymer examples are summarized in Table 21.

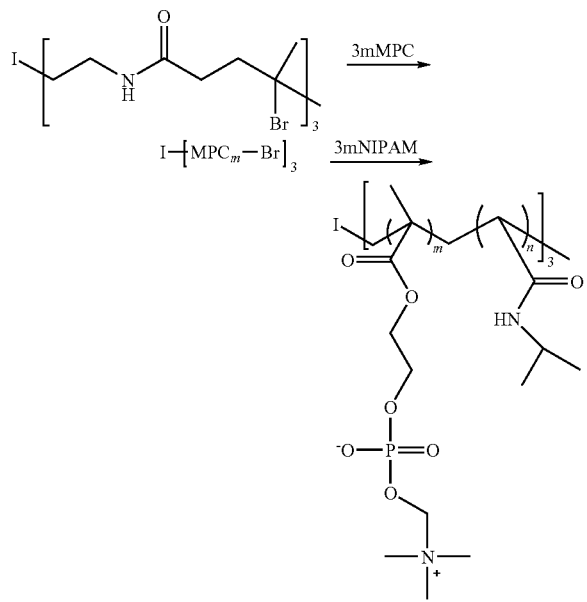

11.4 Thermo-Responsive Gelation Behaviour of Star Diblock Copolymers.

The aqueous gelation behaviour of these star diblock copolymers was investigated at 37° C. in PBS buffer. All three copolymers gelled at 37° C. over a small temperature interval (<1° C.) and at lower copolymer concentrations compared to the ABA triblock copolymers.

was used in all experiments. Temperature dependent changes in G' (storage modulus), G" (loss modulus) were recorded using a controlled temperature ramp. A controlled stress of 1.0 Pa at a frequency of 1.0 rad s⁻¹ and a temperature ramp from 10 to 75° C. were applied. The temperature ramp was increased over 0.3° C./min for heating and 0.6° C./min for cooling. The polymers shown in FIG. 15 were taken from Example 10 and were evaluated as solutions at 6 wt % polymer in PBS. All polymers demonstrate an increase in both G' and G" as the temperature is increased from 10 to 70° C. The behaviour was fully reversible, the curves tracing the exact same line as the temperature was dropped from 70 to 10° C. These data clearly show that Example 10/10, which contains a polypropylene oxide (PPO) component, forms a much stiffer gel upon raising the temperature than the other polymers tested that did not contain the PPO. Examples 10/8 & 10/9 reach a plateau in G" by about 45° C., whereas the maximum G" for Example 10/10 is not reached within the maximum operating temperature of the equipment used use.

FIG. 16 shows the rheological data for thermo-reversible gels based upon NIPAM as described in Example 11. This type of material shows a similar response to increase in temperature to those materials described in Example 10, but the transition from viscous liquid to gel is sharper. A plateau in both G' and G" has not been reached within the operating range of the instrument. The curves for G' and G" upon cooling were again superimposable on the those shown for heating, demonstrating the reversible nature of the transition. The magnitude of the G' and G" values were comparable between Example 10/10 and Example 11.

EXAMPLE 13

Drug Release from Aqueous Block Copolymer Compositions

The polymers of Example 1 with the theoretical composition DPA₅₀MPC₂₅₀DPA₅₀ were dissolved separately in aqueous solvent at pH 2-3 and a concentration of 15% w/v. To the solutions was added dipyridamole at a concentration of 5% by weight based on the weight of polymer. Release of dipyridamole from the acid solutions through a dialysis membrane (which is permeable to drug but not to polymer) was

TABLE 21

Formulation details for the ATRP of NIPAM initiated using the difunctional and trifunctional MPC macro-initiator in an ice bath and summary of the gelation behavior of the various ABA triblock and star-like I-(MPC₁₂₅-NIPAMₙ)₃ diblock copolymers in PBS solutions at 37° C.

| Ex# | ABA triblock and Star diblock copolymer composition | NIPAM mmol | Ig | Cu(I)Br mmol | Me₄cyclam mmol | MeOH ml | Cu ppm | Copolymer conc % w/w in PBS |
|---|---|---|---|---|---|---|---|---|
| 11/1 | NIPAMₘ-MPC₂₀₀-NIPAMₘ | 10.0 | 2.95 | 0.1 | 0.1 | 10 | — | 6.5 |
| 11/2 | NIPAMₘ-MPC₂₅₀-NIPAMₘ | 6.5 | 2.4 | 0.065 | 0.065 | 6.5 | — | 6.5 |
| 11/3 | NIPAMₘ-MPC₃₀₀-NIPAMₘ | 8.0 | 3.54 | 0.08 | 0.08 | 8 | — | 5.8 |
| 11/4 | I-[MPC₁₀₀-NIPAMₘ]₃ | 0.13 | 3.83 | 0.13 | 0.13 | 15 | — | 7.7 |
| 11/5 | I-[MPC₁₂₅-NIPAM₄₈]₃ | 54.0 | 1.0 | 0.027 | 0.027 | 5 | 20.2 | 7.8 |
| 11/6 | I-[MPC₁₂₅-NIPAM₅₁]₃ | 54.0 | 1.0 | 0.027 | 0.027 | 10 | 8.2 | 8.8 |
| 11/7 | I-[MPC₁₂₅-NIPAM₄₇]₃ | 54.0 | 1.0 | 0.027 | 0.027 | 20 | 8.8 | 7.5 |
| 11/8 | I-[MPC₁₅₀-NIPAMₘ]₃ | 10.0 | 4.41 | 0.1 | 0.1 | 20 | — | 6.8 |

EXAMPLE 12

Rheological Studies on Thermo-responsive Gels

Figure 8:
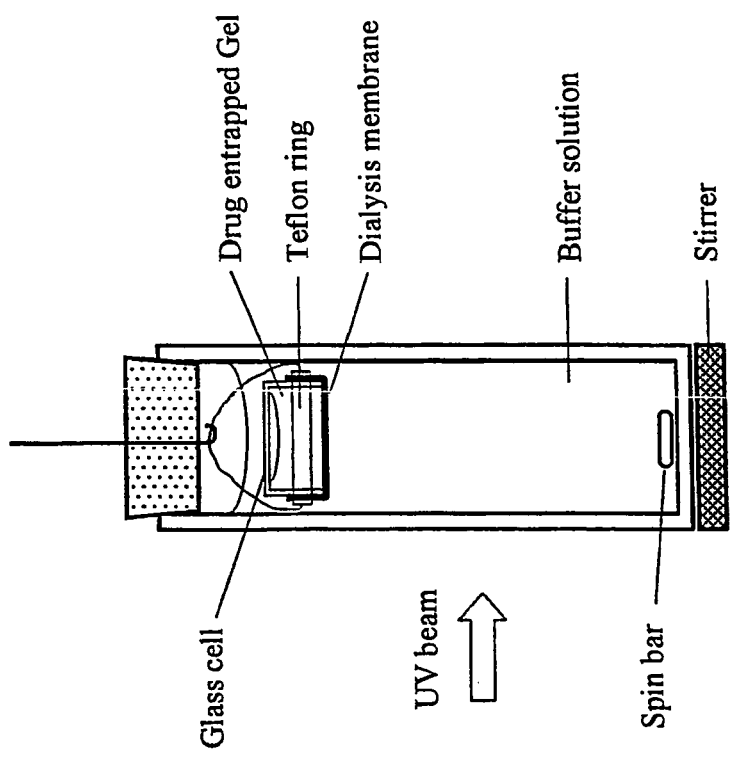
FIG. 8 shows the apparatus used in example 5.
Figure 9:
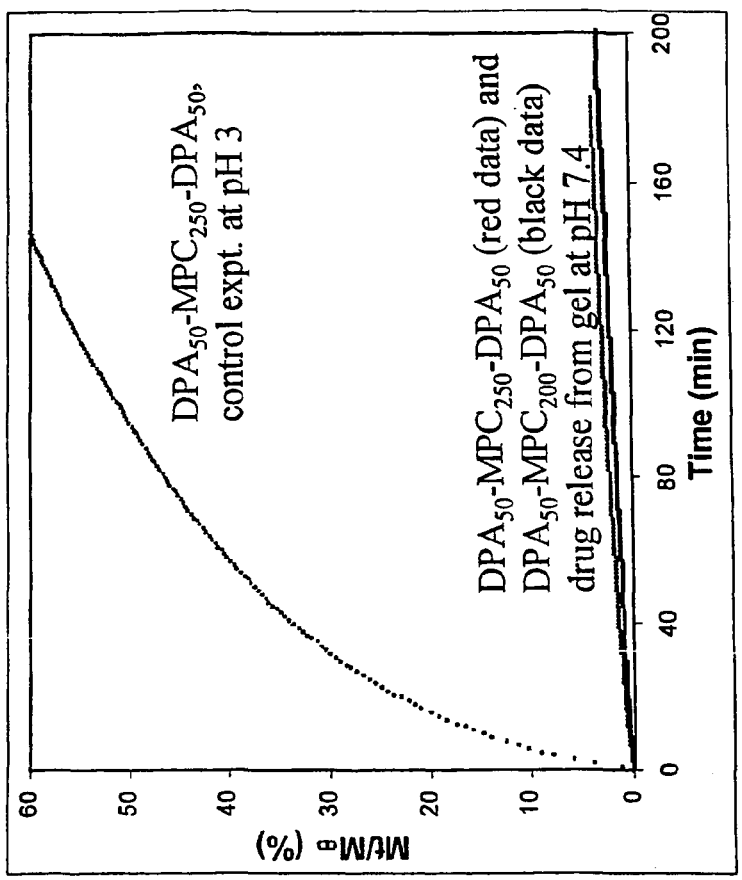
FIG. 9 shows the results of example 5.

Rheological properties of solutions and gels were studied using an CSL 100 (Carri-Med Rheometer. A 1.59°, 6 cm cone compared to release of dipyridamole from the gels formed by adjusting the pH to 7.4. The set up of the release experiment is shown in FIG. 8. Release of drug is determined by fluorescence determination of the solution of the opposite side of the membrane from polymer composition. The results are shown in FIG. 9.

The results show that dipyridamole is released through the membrane from the pH3 solution at a rate such that about 60% is release over 150 min. At pH 7.4 both polymers, which are gelled under these conditions, as shown in Example 1 above, significantly slow down the release of drug.

The invention claimed is:

1. A method in which a liquid composition comprising an aqueous solvent and a block copolymer, in which the block copolymer comprises a hydrophilic core block and at least two terminal blocks, each terminal block being responsive to a stimulus selected from a change in concentration of ions in the composition, imposition of shear, irradiation with electromagnetic radiation, a change in temperature, and a change in pH, in which the blocks are each formed at least in part by the polymerisation of ethylenically unsaturated monomers, wherein the average degree of polymerization of each terminal block is at least 20 characterised in that the core block comprises zwitterionic pendant groups, and has a degree of polymerisation of about 150 up to about 400 is subjected to a stimulus selected from a change in concentration of ions in the composition, imposition of shear, irradiation with electromagnetic radiation, a change in temperature, and a change in pH, to which the terminal blocks respond, whereby the terminal blocks respond to the stimulus to form a gel.

2. A method according to claim 1 in which the monomers from which the core block is formed comprise compounds of the general formula I

Y—B—X    I in which Y is an ethylenically unsaturated group selected from $H_2C=CR-CO-A-$, $H_2C=CR-C_6H_4-A^1-$, $H_2C=CR-CH_2A^2$, $R^2O-CO-CR=CR-CO-O$, $RCH=CH-CO-O-$, $RCH=C(COOR^2)CH_2-CO-O$,

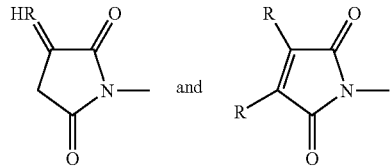

A is —O— or $NR^1$;
$A^1$ is selected from a bond, $(CH_2)_lA^2$ and $(CH_2)_lSO_3-$ in which l is 1 to 12;
A2 is selected from a bond, —O—, O—CO—, CO—O, CO—NR1—, —NR1—CO, O—CO—NR1—, NR1-CO—O—;
R is hydrogen or C1-4 alkyl;
R1 is hydrogen, C1-4-alkyl or BX;
R2 is hydrogen or C1-4 alkyl;
B is a bond, or a straight branched alkanediyl, alkylene oxaalkylene, or alkylene (oligooxalkylene) group, optionally containing one or more fluorine substituents;
X is a zwitterionic group.

3. A method according to claim 2 in which X is a group of the general formula II

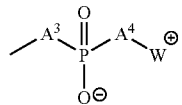

II in which the moieties $A^3$ and $A^4$, which are the same or different, are —O—, —S—, —NH— or a valence bond, and $W^+$ is a group comprising an ammonium, phosphonium or sulphonium cationic group and a group linking the anionic and cationic moieties.

4. A according to claim 1 in which the monomers from which the terminal blocks are formed comprise compounds of the formula VI

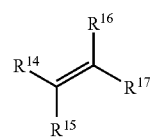

VI where $R^{14}$ is selected from the group consisting of hydrogen, halogen, $C_{1-4}$ alkyl and groups $COOR^{18}$ in which $R^{18}$ is selected from the group consisting of hydrogen and $C_{1-4}$ alkyl;
$R^{15}$ is selected from the group consisting of hydrogen, halogen and $C_{41-}$ alkyl;
$R^{16}$ is selected from the group consisting of hydrogen, halogen, $C_{1-4}$ alkyl and groups $COOR^{18}$ provided that $R^{14}$ and $R^{16}$ are not both $COOR^{18}$
or $R^{14}$ and $R^{16}$ may together form $CONR^{19}CO$ in which $R^{19}$ is a $C_{1-20}$ alkyl group; and
$R^{17}$ is selected from the group consisting of $C_{1-10}$ alkyl, $C_{1-20}$ alkoxycarbonyl, mono- and di-($C_{1-20}$ alkyl)amino carbonyl, $C_{6-20}$ aryl, $C_{7-20}$ aralkyl, $C_{6-20}$ aryloxy carbonyl, $C_{7-20}$ aralkoxyl carbonyl, $C_{6-20}$ arylamino carbonyl, $C_{7-20}$ aralkyl amino carbonyl, $C_{2-20}$ aralkylamino and $C_{2-10}$ acyloxy groups, in which an alkyl or aryl group has a substituent which is responsive to a stimulus and in which any of the alkyl or aryl groups may additionally be substituted by one or more substituents selected from halogen atoms, alkoxy, oligo-alkoxy, aryloxy, acyloxy, acylamino, amine, carboxyl, sulphonyl, phosphoryl, phosphino, zwitterionic, hydroxyl groups, vinyloxycarbonyl and other vinylic or allylic substituents, and reactive silyl or silyloxy groups.

5. A method according to claim 4 in which the stimulus responsive substituent is a proton donor or proton acceptor.

6. A method according to claim 5 in which the stimulus responsive substituent comprises a group selected from carboxylic, carboxylate, $SO_3H$, $SO_3-$, $PO_3HR^{20}$ and $PO_2-R^{20}$ and $PO_3^{2-}$, in which $R^{20}$ is selected from the group consisting of hydroxyl, $C_{1-12}$ alkyl $C_{1-12}$ alkoxy, $C_{6-18}$ aryl, $C_{6-18}$ aryloxy, $C_{7-18}$ aralkyl and $C_{7-18}$ aralkoxy.

7. A method according to claim 5 in which the stimulus responsive substituent is selected from the group consisting of $NR^{21}_2$, $N^+R^{21}_2H$, $PR^{22}_2$, $P^+R^{22}_2H$, $SR^{21}$, $S^+R^{21}H$, wherein the or each group $R^{21}$ is selected from the group consisting of hydrogen, optionally substituted $C_{1-20}$ alkyl and aryl, or the two groups $R^{21}$ are joined to form, together with the heteroatom to which they are each attached, a 5-7 membered heterocycle, and each $R^{22}$ is $R^{21}$ or $OR^{21}$.

8. A method according to claim 7 in which the compound of the formula VI is ω-(N,N-dialkylamino)alkyl-(alk)acrylate or (alk)acrylamide.

9. A method according to claim 1 in which the monomers from which each terminal block and/or the core block is formed comprise comonomers, selected from compounds of the general formula VII

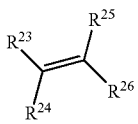

in which $R^{23}$ is selected from the group consisting of hydrogen, halogen, $C_{1-4}$ alkyl and groups $COOR^{27}$ in which $R^{27}$ is hydrogen and $C_{1-4}$ alkyl;

$R^{24}$ is selected from the group consisting of hydrogen, halogen and $C_{1-4}$ alkyl;

$R^{25}$ is selected from the group consisting of hydrogen, halogen, $C_{1-4}$ alkyl and groups $COOR^{27}$ provided that $R^{23}$ and $R^{25}$ are not both $COOR^{27}$; and $R^{26}$ is selected from the group consisting of $C_{1-10}$ alkyl, $C_{1-20}$ alkoxycarbonyl, mono- and di-($C_{1-20}$ alkyl)amino carbonyl, $C_{6-20}$ aryl (including alkaryl), $C_{7-20}$ aralkyl, $C_{6-20}$ aryloxycarbonyl, $C_{7-20}$-aralkyloxycarbonyl, $C_{6-20}$ arylamino carbonyl, $C_{7-20}$ aralkyl-amino carbonyl, hydroxyl and carboxylic $C_{2-10}$ acyloxy groups, any of which may have one or more substituents selected from the group consisting of halogen atoms, alkoxy, oligo-alkoxy, aryloxy, acyloxy, acylamino, amine, carboxyl, sulphonyl, phosphoryl, phosphino, zwitterionic, hydroxyl, vinyloxycarbonyl and other vinylic and allylic groups, and reactive silyl and silyloxy groups;

or $R^{26}$ and $R^{25}$ or $R^{25}$ and $R^{23}$ may together form —$CONR^{28}CO$ in which $R^{28}$ is a $C_{1-20}$ alkyl group.

10. A method according to claim 1 in which the polydispersity of block weight of the core block is in the range 1.1 to 2.0.

11. A method according to claim 1 in which the mean degree of polymerisation of the terminal blocks is in the range 30 to 100.

12. A method according to claim 1 in which the polydispersity of block weight of the terminal blocks is in the range 1.1 to 3.0.

13. A method according to claim 1 in which the ratio of the mean degree of polymerisation of the core block to the mean degree of polymerisation of each of the terminal blocks is in the range 20:1 to 1:1.

14. A method according to claim 5 in which the substituent is a proton acceptor having a pH more than the $pK_A$ of the conjugate acid of the said substituent.

15. A method according to claim 5 in which the substituent is a proton acceptor, having a pH less than the $pK_A$ of the conjugate acid of the substituent.

16. A method according to claim 5 in which the substituent is a proton donor having a pH more than the $pK_A$ of the substituent.

17. A method according to claim 5 in which the substituent is a proton donor, having a pH less than the $pK_A$ of the substituent.

18. A method according to claim 1 in which the composition comprises a biologically active agent.

19. A method according to claim 1 in which the composition comprises an imaging agent.

20. A method according to claim 1 in which the composition has an A-B-A structure, the B block being the core block and the A blocks being the terminal blocks.

21. A method according to claim 1 in which the stimulus is subsequently removed, whereupon the mechanical characteristics of the composition revert at least in part to their original values.

22. A method according to claim 1 in which the stimulus is a change in the pH.

23. A method according to claim 1 in which the stimulus is selected from the group consisting of temperature change, shear, change in dissolved ion concentration and electromagnetic irradiation.

24. A according to claim 3 in which W⁺ is a group of formula

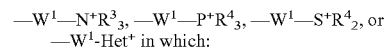
—W¹-Het⁺ in which:

W¹ is alkanediyl of 1 or more carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group W1 optionally contains one or more fluorine substituents and/or one or more functional groups; and either the groups $R^3$ are the same or different and each is hydrogen or alkyl of 1 to 4 carbon atoms, or two of the groups $R^3$ together with the nitrogen atom to which they are attached form an aliphatic heterocyclic ring containing from 5 to 7 atoms, or the three groups $R^3$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^3$ is substituted by a hydrophilic functional group, and the groups $R^4$ are the same or different and each is $R^3$ or a group $OR^3$, where $R^3$ is as defined above; or Het is an aromatic nitrogen-, phosphorus- or sulphur-containing ring.

25. A method according to claim 1 in which the composition comprises a solvent and a block copolymer, and in which the block copolymer has an A-B-A structure, wherein the B block is formed by polymerising ethylenically unsaturated monomers comprising a compound of the formula I $$Y\text{—}B\text{—}X \qquad\qquad I$$

wherein Y is $H_2C=CR$—CO-A, R is H or $C_{1-4}$ alkyl, A is O or NH, B is $C_{2-6}$-alkanediyl and X is

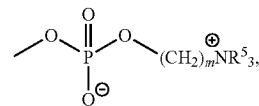

M is 1 to 4 and each $R^5$ is H or $C_{1-4}$ alkyl, to an average degree of polymerisation or at least 100; and each A block is formed by polymerising ethylenically unsaturated monomers including a compound of the formula VI

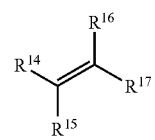

wherein $R^{14}$ and $R^{15}$ are H, $R^{16}$ is H or $C_{1-4}$ alkyl and $R^{17}$ is a $C_{1-20}$ alkoxycarbonyl or a mono- or di-($C_{1-20}$) alkylaminocarbonyl group having a $NR^{21}_2$ substituent wherein the $R^{21}$ groups are alkyl groups, to an average degree of polymerisation of at least 20.

26. A method according to claim 25 wherein the compound of formula I is 2-methacryloyloxy-ethyl-2'-trimethylammoniamethyl phosphate inner salt and the compound of formula VI is a dialkylaminoalkyl(alk)acrylate.

27. A method according to claim 26 in which the compound of formula VI is diisopropylaminoethylmethacrylate, or dimethylaminoethylmethacrylate.

28. A method comprising a solvent and a block copolymer, in which the block copolymer has an A-B-A structure, wherein the B block is formed by polymerising ethylenically unsaturated monomers comprising a compound of the formula I

Y—B—X    I wherein Y is $H_2C$=CR—CO-A, R is H or $C_{1-4}$ alkyl, A is O or NH, B is $C_{2-6}$-alkanediyl and X is

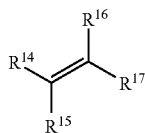

M is 1 to 4 and each $R^5$ is H or $C_{1-4}$ alkyl, to an average degree of polymerisation or at least 100; and each A block is formed by polymerising ethylenically unsaturated monomers including a compound of the formula VI

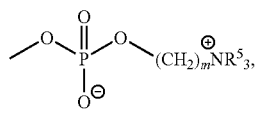

wherein $R^{14}$ and $R^{15}$ and H, $R^{16}$ is H or $C_{1-4}$ alkyl, and $R^{17}$ is a $C_{1-20}$ alkylcarbonyl or a mono- or di-$C_{1-20}$ alkylaminocarbonyl group having a hydroxyl substituent.

29. A method according to claim 28 wherein the compound of formula I is 2-methacryloyloxy-ethyl-2'-trimethylammoniamethyl phosphate inner salt and the compound of formula VI is hydroxyethylmethacrylate.

30. A method according to claim 1 in which the composition comprises a solvent and a block copolymer, and in which the block copolymer has an A-B-A structure, wherein the B block is formed by polymerising ethylenically unsaturated monomers comprising a compound of the formula I

Y—B—X    I wherein Y is $H_2C$=CR—CO-A, R is H or $C_{1-4}$ alkyl, A is O or NH, B is $C_{2-6}$-alkanediyl and X is

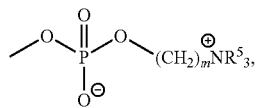

M is 1 to 4 and each $R^5$ is H or $C_{1-4}$ alkyl, to an average degree of polymerisation or at least 100; and each A block is formed by polymerising ethylenically unsaturated monomers including a compound of the formula VI

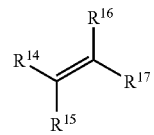

wherein $R^{14}$ and $R^{15}$ are H, $R^{16}$ is H or $C_{1-4}$ alkyl, and $R^{17}$ is a $C_{1-20}$ alkylcarbonyl or a mono- or di-$C_{1-20}$ alkylaminocarbonyl group having a N-morpholino group substituent.

31. A method according to claim 1 in which the composition comprises a solvent and a block copolymer, and in which the block copolymer has an A-B-A structure, wherein the B block is formed by polymerising ethylenically unsaturated monomers comprising a compound of the formula I

Y—B—X    I wherein Y is $H_2C$=CR—CO-A, R is H or $C_{1-4}$ alkyl, A is O or NH, B is $C_{2-6}$-alkanediyl and X is

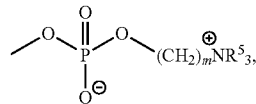

M is 1 to 4 and each $R^5$ is H or $C_{1-4}$ alkyl, to an average degree of polymerisation or at least 100; and each A block is formed by polymerising ethylenically unsaturated monomers including a compound of the formula VI

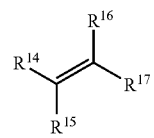

wherein $R^{14}$ and $R^{15}$ are H, $R^{16}$ is H or $C_{1-4}$ alkyl, and $R^{17}$ is a N-isopropylaminocarbonyl.

32. A method according to claim 8 in which the compound of formula VII is ω-(N,N-dialkylamino)alkyl-(alk)acrylate.

33. A method according to claim 32 in which the compound of formula VII is 2-(diisopropyl amino)ethyl methacrylate.

34. A method according to claim 4 in which the silyloxy groups are trialkoxysilyl groups.

35. A method according to claim 9 in which the silyloxy groups are trialkoxysilyl groups.

* * * * *